(12) United States Patent
Denison et al.

(10) Patent No.: US 10,500,074 B2
(45) Date of Patent: Dec. 10, 2019

(54) DEFORMABLE LUMEN SUPPORT DEVICES AND METHODS OF USE

(71) Applicant: CELONOVA STENT, INC., San Antonio, TX (US)

(72) Inventors: Andy Edward Denison, Temecula, CA (US); Kent C. B. Stalker, San Marcos, CA (US)

(73) Assignee: CELONOVA STENT, INC., Peachtree City, GA (US)

( * ) Notice: Subject to any disclaimer, the term of this patent is extended or adjusted under 35 U.S.C. 154(b) by 126 days.

(21) Appl. No.: 15/338,937

(22) Filed: Oct. 31, 2016

(65) Prior Publication Data

US 2017/0042706 A1 Feb. 16, 2017

Related U.S. Application Data

(60) Division of application No. 13/595,956, filed on Aug. 27, 2012, now Pat. No. 9,510,960, which is a continuation of application No. 13/347,685, filed on Jan. 10, 2012, now abandoned, which is a continuation of application No. 11/875,718, filed on Oct. 19, 2007, now abandoned.

(60) Provisional application No. 60/853,245, filed on Oct. 21, 2006.

(51) Int. Cl.
*A61F 2/844* (2013.01)
*A61F 2/91* (2013.01)
*A61F 2/915* (2013.01)
*A61F 2/958* (2013.01)
*A61F 2/82* (2013.01)

(52) U.S. Cl.
CPC ............ *A61F 2/844* (2013.01); *A61F 2/91* (2013.01); *A61F 2/915* (2013.01); *A61F 2/958* (2013.01); *A61F 2002/828* (2013.01); *A61F 2002/91558* (2013.01); *A61F 2002/91566* (2013.01); *Y10T 29/49925* (2015.01)

(58) Field of Classification Search
CPC .. A61F 2/958; A61F 2/966; A61F 2/95; A61F 2/07; A61F 2/82
See application file for complete search history.

(56) References Cited

U.S. PATENT DOCUMENTS

| | | |
|---|---|---|
| 6,488,702 B1 | 12/2002 | Besselink |
| 6,942,690 B1 | 9/2005 | Pollock |
| 7,235,097 B2 | 6/2007 | Calisse |
| 2002/0072792 A1 | 6/2002 | Burgermeister |
| 2002/0107562 A1* | 8/2002 | Hart ............... E21B 43/106 623/1.15 |
| 2002/0107563 A1 | 8/2002 | Shanley |
| 2003/0204239 A1 | 10/2003 | Carlyle |

(Continued)

FOREIGN PATENT DOCUMENTS

| | | |
|---|---|---|
| WO | 98/32412 | 7/1998 |
| WO | 2007/076051 | 7/2007 |

*Primary Examiner* — Christopher D. Prone
*Assistant Examiner* — Tiffany P Shipmon
(74) *Attorney, Agent, or Firm* — Mannava & Kang, P.C.; Carol L. Bunner

(57) ABSTRACT

Lumen support devices and methods of their use are provided. A lumen support includes one or more plastically deformable cells having two stable configurations with no stable configurations between the two stable configurations. The lumen support device may be plastically deformed to other stable configurations.

16 Claims, 24 Drawing Sheets

(56) References Cited

U.S. PATENT DOCUMENTS

2004/0193247 A1 9/2004 Besselink
2005/0267560 A1* 12/2005 Bates .................. A61F 2/2418
                                                                 623/1.1
2006/0235506 A1 10/2006 Ta et al.

* cited by examiner

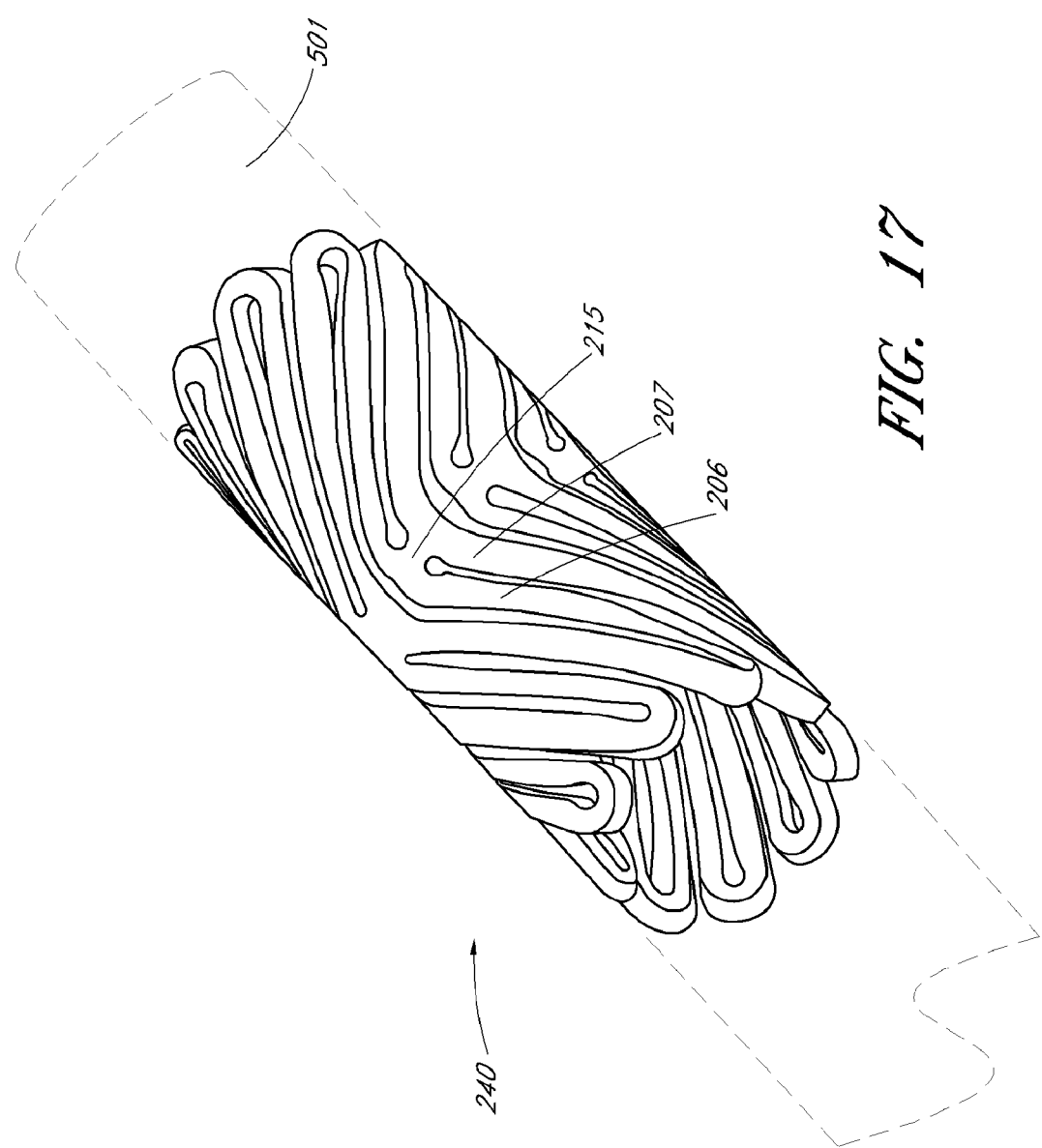

DEFORMABLE LUMEN SUPPORT DEVICES AND METHODS OF USE

CROSS-REFERENCE TO RELATED APPLICATIONS

This application claims the priority benefit under 35 U.S.C. § 119(e) of the provisional application 60/853,245, filed Oct. 21, 2006 which is hereby incorporated by reference in its entirety.

BACKGROUND OF THE INVENTION

Field of the Invention

Embodiments described herein relate to lumen supports having plastically deformable structures.

Description of Related Technology

Vascular prostheses, commonly referred to as stents, are now widely used in interventional procedures for treating lesions of the coronary arteries and other vessels. Such devices generally have a tubular shape and are deployed in a vessel, and are intended to restore and maintain the patency of a segment of a vessel. Previously-known vascular prostheses are generally either self-expanding or balloon expandable, and may vary in size, shape or other characteristics depending on whether the use is for the cardiac vasculature, carotid arteries, renal arteries, superficial femoral arteries, or other vessels.

Self-expanding and balloon expandable stents often have elasticities associated with a relatively large amount of recoil. As such, the stent may be prone to recoil inward after being expanded to its maximum outer diameter. If this recoil is significant, the stent may not remain stationary relative to the passageway, instead migrating to a point of lesser desirability. As a result, serious or fatal injury to the patient may occur.

Another aspect of stents is the size to which they may be compacted through crimping. Stents may be crimped onto a catheter for delivery to a lesion location within a lumen. One manner of crimping involves the application of a force directed in a radially inward direction to force the stent into a compact profile. However, the stent's diameter may tend to recoil to a diameter greater than its minimum diameter. This recoil typically increases as the material's elasticity increases. One disadvantage of this phenomenon is that, with increased recoil after crimping, the stent's delivery profile is increased, thereby limiting the stent's applicability to small vessels that would otherwise be accessible by a stent with a smaller delivery profile. Another disadvantage is that a stent that is not tightly coupled to the delivery catheter may become dislodged at an undesirable location during delivery.

Different material choices for stents or other medical devices offer different advantages and disadvantages. For example, some highly elastic materials have increased strength and/or increased radiopacity when compared to other materials with a lower elasticity, yet suffer from greater recoil than materials with a lesser elasticity. A balance is desired in which beneficial features of such stent materials may be enjoyed while reducing disadvantages such as recoil.

SUMMARY OF THE INVENTION

In view of the foregoing drawbacks of previously-know vascular prostheses and other similar medical devices, one aspect of certain embodiments described herein is to provide a lumen support having one or more unit cells. In particular embodiments, the one or more unit cells are capable of assuming multiple stable configurations. In one aspect of certain embodiments, the lumen support having the one or more multistable unit cells comprises beneficial features of elastic materials. Another aspect of certain embodiments is to provide a lumen support having one or more multistable cells that do not significantly increase in diameter due to recoil following crimping. Yet another object of certain embodiments is to provide a lumen support that does not significantly decrease in diameter due to recoil following expansion.

These and other advantages are achieved by providing a supportive structure having a body comprising a plurality of cells capable of low recoil due to some reversal of elastic strain when crimped. The cells further may undergo plastic deformation as the medical device is deployed into an expanded configuration, and the asymmetrical shape of the cells reduces the degree of recoil in comparison to known stent designs. In certain embodiments, such a supportive structure is well-adapted to be formed of certain elastic materials such as cobalt alloys and stainless steel, thereby being capable of enjoying the advantages of strength and/or radiopacity, with a reduction in effects such as recoil.

In one embodiment, a lumen support is configured to be expanded and contracted to a plurality of stable positions. In some embodiments, the support includes a plurality of cells. In some embodiments, each of the plurality of cells is defined by at least a first segment and a second segment. In some embodiments, the cell includes a first stable collapsed configuration, a second stable collapsed configuration, a first stable expanded configuration, and a second stable expanded configuration. In certain embodiments, the first segment, is made of a material having an elastic range of between about 0.15 to about 1% and an elongation of above 30% and an ultimate tensile strength greater than 500 MPa. As discussed further herein, the strut made of this material exhibits reduced recoil to an applied force. In some embodiments, the second segment is less flexible than the first segment. In certain embodiments, the first segment may transition from a first stable contracted position to a first stable expanded position relative to said second segment. This transition causes the cell to transition from the first stable collapsed configuration to the first stable expanded configuration. In some embodiments, the first segment is configured to plastically deform to a second stable contracted position creating an area for each cell less than the area created when said first segment is at said first stable contracted position. In some embodiments, the first segment is configured to plastically deform to a second stable expanded position creating an area for each cell greater than the area created when said first segment is at said first stable expanded position. In some embodiments, the first segment is configured to transition between contracted and expanded positions through an inversion point in which force is reduced in order to complete the transition. In some embodiments, the first segment has an elastic range of between about 0.3 to about 0.8%. In some embodiments, the first segment substantially conforms to the shape of the second segment in the first stable collapsed configuration. In some embodiments, the second segment comprises a plastically deformable segment made of the material of the first segment.

In another embodiment, a lumen support includes a plastically deformable structure made of a material having an elastic range between about 0.15 to about 1% and an elongation of above 30% and an ultimate tensile strength greater than 500 MPa. Such structure is capable of assuming an original collapsed configuration or a plastically deformed collapsed configuration and an original expanded configuration or a plastically deformed expanded configuration, wherein no stable configurations exist between the original collapsed configurations or the original expanded configuration. In certain embodiments, the structure is defined in part by a first segment and a second segment, the first segment being more flexible than the second segment. In certain embodiments, the first segment is capable of transitioning between a contracted position and an expanded position, relative to the second segment, wherein the first segment passes a transition point between the contracted position and the expanded position that allows force to be decreased during the transition.

In another embodiment, a method of crimping a lumen support on a delivery device is described. Such method may include delivering a lumen support onto a delivery device. Lumen supports are further discussed herein and can be used with any embodiment or feature of any lumen support described herein. The method may further include applying a radially inward force to the lumen support, and deforming one or more unit cells of the lumen support to a plastically deformed collapsed configuration. In certain embodiments, the method may include transitioning the lumen support to a stable collapsed configuration from a stable expanded configuration by application of a force through an inversion point of decreased force. In one embodiment, the lumen support has a smaller diameter in the plastically deformed collapsed configuration than in the stable collapsed configuration. In one embodiment, the lumen support includes a first segment and a second segment, the first segment being more pliable than the second segment. In certain embodiments, the lumen support includes a material having an elastic range between about 0.15 to about 1% and an elongation of above 30% and an ultimate tensile strength greater than 500 MPa.

In another embodiment, a lumen support includes a plurality of unit cells arranged in a first column and a second column, the first and second columns having a tubular shape and being interconnected by at least one flexible connector. In some embodiments, each unit cell in the first column of unit cells is coupled by first flexible articulations. In some embodiments, each unit cell in the second column of unit cells is coupled by second flexible articulations. In some embodiments, at least some of the unit cells of the plurality of unit cells are capable of transitioning between a stable expanded configuration and a stable collapsed configuration by application of a force through an inversion point of decreased force. In some embodiments, the first flexible articulations and the flexible connector are configured to allow one or more unit cells of the first column to conform to a lumen. In certain embodiments, the plurality of unit cells is made of a material having an elastic range between about 0.15 to about 1% and an elongation of above 30% and an ultimate tensile strength greater than 500 MPa. In some embodiments, the material is a cobalt alloy or is stainless steel.

In another embodiment, a balloon catheter includes a balloon and a lumen support device in a crimped configuration coupled to the balloon. In one embodiment, the device includes one or more unit cells capable of transitioning from a stable collapsed configuration to a stable expanded configuration by application of a force through an inversion point of decreased force. In some embodiments, the one or more unit cells are capable of plastically deforming to an expanded plastically deformed configuration. In some embodiments, the lumen support device includes a material having an elastic range between about 0.15 to about 1% and an elongation of above 30% and an ultimate tensile strength greater than 500 MPa. In some embodiments, the material is a cobalt alloy.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 17 is a drawing of a crimped stent;

DETAILED DESCRIPTION OF THE PREFERRED EMBODIMENT

Figure 1:
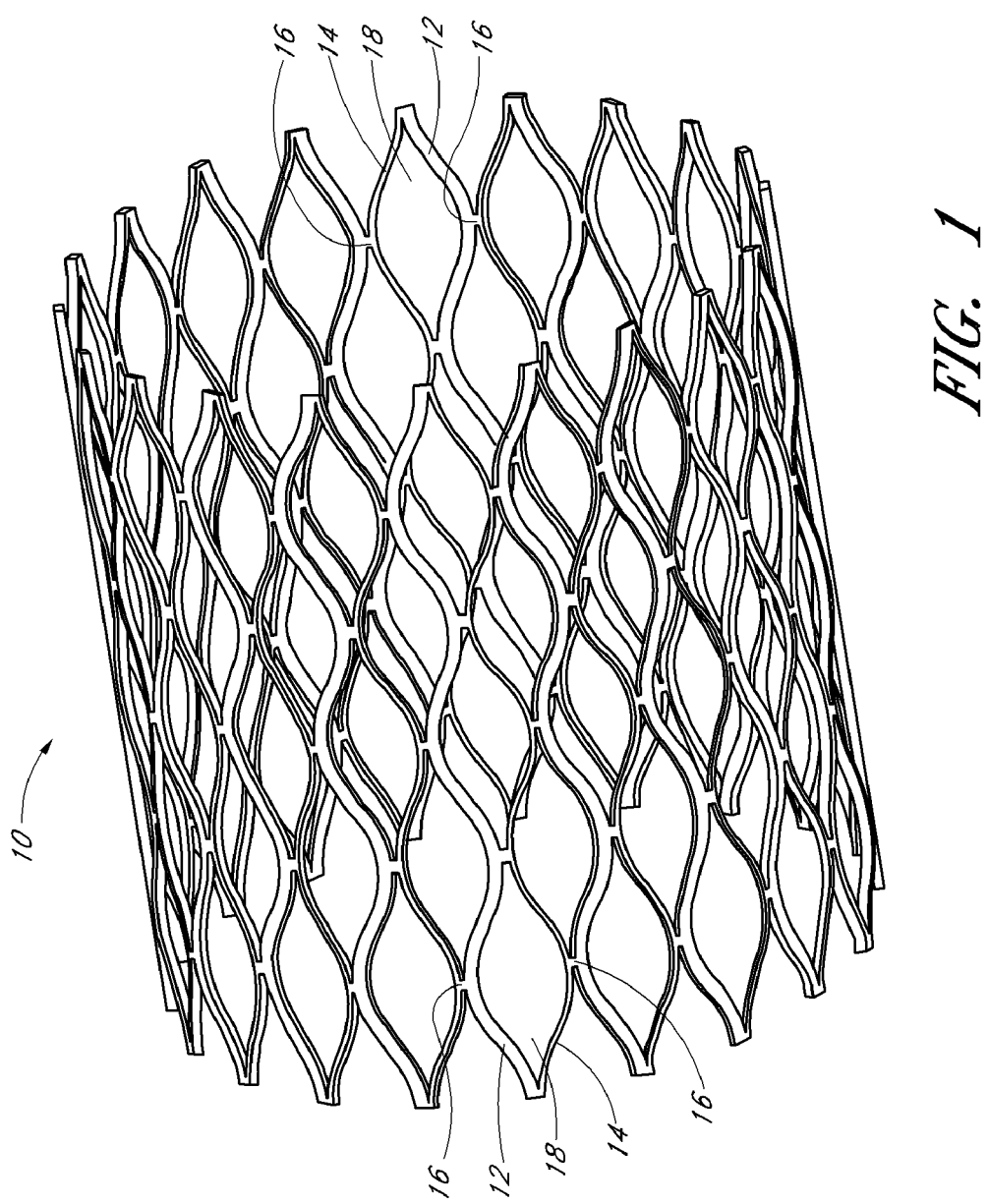
FIG. 1 is a supportive structure in a stable expanded configuration in accordance with one embodiment.

Certain embodiments include a supportive structure that comprises one or more cells having a stable collapsed configuration and a stable expanded configuration. In particular embodiments, the supportive structure may be at least a part of a medical device. Unless otherwise indicated, the term "medical device" is a broad term and is used in its ordinary sense and includes, without limitation, wherein the context permits, stents, stent delivery devices, valves, multi-stable valves, occlusion devices, expanders, clips, loops, rings, and other devices including cells, whether open or closed. In particular embodiments, the supportive structure comprises one or more cells in a tubular form. In certain embodiments, a tubular device is described in terms of "diameter" of a portion of the tubular structure. While tubular embodiments having circular cross-sections (e.g., of constant diameter along its length) are sometimes preferred, other embodiments are not limited to that geometry. As such devices within the scope of the present invention may also include tapered portions, conical flares, curved portions, branches, or have other similar geometrical features known in the art.

An example of such a supportive structure is shown in U.S. Pat. No. 6,488,702 (also referred to herein as "the Besselink patent"), which is hereby incorporated by reference in its entirety. Notably, the Besselink patent describes bistable and multistable devices that have two or more stable configurations. In particular, the Besselink patent describes a device having one or more unit cells having a stable collapsed configuration and a stable expanded configuration. As a cell transitions from the stable collapsed configuration to the stable expanded configuration, the cell transitions through a transition point at which the force required to complete the transition is decreased.

In contrast to the Besselink patent, a supportive structure of certain embodiments described herein may be deformably collapsed or expanded to a continuous range of discrete diameters less than or greater than the diameter of the stable collapsed configuration or the stable expanded configuration of the device. As such, devices described herein may include one or more unit cells that have stable collapsed and expanded configurations. Such configurations elastically resist minor deformations. As noted, the cell may transition from a stable collapsed configuration to a stable expanded configuration through a transition point of decreased force. The transition point allows the stent to assume the opposite configuration without additional application of force. Such expansion or contraction may be defined as isothermal in certain embodiments. Once in a stable configuration, whether collapsed or expanded, the cell may then be plastically deformed to an expanded or reduced area. Following such plastic deformation, some degree of recoil results in the unit cell assuming a plastically deformed configuration.

As used herein, the phrase "predetermined stable state" or "predetermined stable configuration" describes a configuration in which one or more cells of the device are in a known configuration that elastically resists change in a manner such that the cell returns to the known configuration following minor deformations. As an example, a bistable cell of the Besselink patent may have two predetermined stable configurations, an open configuration and a closed configuration. Such predetermined configurations may be determined upon manufacture of the device. A cell may "snap" from one configuration to the other in response to a threshold force that displaces a portion of the cell beyond an intermediate or transition point. These configurations are not only stable, but are predetermined based on the design of the cell. In certain embodiments, a predetermined stable configuration may also include a plastically deformed configuration after recoil. As such, where context permits, predetermined may also be used to describe a plastically deformed configuration.

In certain embodiments, the plastically deformed state of one or more cells may be described in terms of increased or decreased area of the unit cell. In some embodiments, the one or more unit cells may be plastically deformed from the original stable collapsed configuration having a first area to a plastically deformed stable collapsed configuration having a second area less than the first area. Likewise, the one or more unit cells may be plastically deformed from the original stable expanded configuration having a first area to a plastically deformed stable expanded configuration having a second area greater than the first area.

Once plastically deformed in one configuration, the one or more unit cells assume the plastically deformed configuration as one of the two stable configurations of the unit cell. For example, a cell that has been plastically deformed from the original stable expanded configuration to a plastically deformed stable expanded configuration will assume the plastically deformed stable configuration of the cell. In some embodiments, such a cell may be capable of transitioning back to a collapsed configuration by applying requisite force to the cell. Likewise, according to some embodiments, the one or more unit cells may be plastically deformed to a plastically deformed collapsed position by crimping, and then expanded to the predetermined stable expanded configuration or beyond into a range of plastic deformation. In certain embodiments, a plastically deformed cell may be further plastically deformed as desired and where the structural integrity of the cell permits.

In certain embodiments, the medical device having the one or more cells is made of an elastic material having certain mechanical and physical properties. Applicants have unexpectedly discovered that certain materials may resist recoil upon being compressed or collapsed or expanded to a plastically deformed state when used in combination with the geometry and structure of unit cells described herein. In particular embodiments, optimal materials may include materials having certain ultimate tensile strengths, elongation percentages, and/or elastic ranges. In certain embodiments, one material used in forming the medical device has an ultimate tensile strength of greater than about 500 MPa, an elongation of greater than about 30%, and an elastic range between about 0.15 and about 1%. In certain embodiments, one material used in forming the medical device has an ultimate tensile strength between about 500 MPa and about 2000 MPa, an elongation of greater than about 25%, and an elastic range between about 0.15% and about 0.8%. Other potential ranges for materials are further described below.

In some embodiments, the material may have an elastic range that is greater than or equal to about 0.20%. In certain embodiments, the one or more cells are made of an elastic material having an elastic range of between about 0.15% and about 0.8%. In certain embodiments, the one or more cells are made of an elastic material having an elastic range of between about 0.2% and about 0.7%. In certain embodiments, the one or more cells are made of an elastic material having an elastic range of between about 0.3% and about 0.9%. In certain embodiments, the one or more cells are made of an elastic material having an elastic range of between about 0.2% and about 0.6%.

In some embodiments, the material may have an ultimate tensile strength that is greater than or equal to about 500 MPa. In certain embodiments, the one or more cells are made of a material having an ultimate tensile strength of between about 450 MPa and about 2000 MPa. In certain embodiments, the one or more cells are made of a material having an ultimate tensile strength of between about 600 MPa and about 1500 MPa. In certain embodiments, the one or more cells are made of a material having an ultimate tensile strength of between about 550 MPa and about 1200 MPa. In certain embodiments, the one or more cells are made of a material having an ultimate tensile strength between about 650 MPa and about 1000 MPa.

In some embodiments, the material may have an elongation that is greater than or equal to about 30%. In certain embodiments, the one or more cells are made of a material having an elongation of between about 25 and about 75%. In certain embodiments, the one or more cells are made of a material having an elongation of between about 30% and about 60%. In certain embodiments, the one or more cells are made of a material having an elongation of between about 35% and about 55%.

It will be appreciated that examples of suitable materials falling within these ranges include cobalt alloys. In some embodiments, cobalt nickel chromium alloys may be used. In some embodiments, cobalt chromium nickel alloys may be used. Nonlimiting examples of such cobalt alloys include, but are not limited to L-605 or MP35N. In certain embodiments, cobalt-chromium alloy is a suitable material to use in forming stents or other medical devices, as it has greater radiopacity than other materials commonly used to form stents. As such, a smaller amount of cobalt-chromium alloys may be used compared to other known materials. While some embodiments include unit cells made in part of cobalt-chromium alloy, embodiments may also be practiced with materials having similar mechanical properties as described herein. In one nonlimiting embodiments, a stainless steel alloy may be used. In particular, a stainless steel alloy may include 316 SS. Other suitable materials may include polymeric materials or bioabsorbable materials. Physical and mechanical properties of the above-mentioned suitable materials are found in Table 1, copied from Poncin, P. et al., Stent Tubing: Understanding the Desired Attributes, Materials & Processes for Medical Devices Conference, September 2003, which is hereby incorporated by reference in its entirety.

TABLE 1

Physical and mechanical properties of selected materials.

| | DENSITY gr/cm$^3$ | ELASTIC MODULUS G Pa | ULTIMATE TENSILE STRENGTH MPa | 0.2% YIELD STRENGTH MPa | UTS-YIELD MPa | ELONG. % | ELASTIC RANGE % |
|---|---|---|---|---|---|---|---|
| STAINLESS STEELS | | | | | | | |
| Fe—18Cr—14Ni—2.5Mo "316LVM" ASTM F138 | 7.95 | 193 | 670 | 340 | 330 | 48 | 0.17 |
| Fe—21Cr—10Ni—3.5Mn—2.5Mo ASTM F 1586 | 7.90 | 195 | 740 | 430 | 310 | 35 | 0.22 |
| Fe—22Cr—13Ni—5Mn ASTM F 1314 | 7.88 | 193 | 827 | 448 | 379 | 45 | 0.23 |
| Fe—23Mn—21Cr—1Mo—1N Nickel free SS | 7.63 | 190 | 931 | 607 | 324 | 49 | 0.32 |
| COBALT ALLOYS | | | | | | | |
| Co—20Cr—15W—10Ni "L605" ASTM F90 | 9.10 | 243 | 820-1200 | 380-780 | 420-600 | 35-55 | 0.16-0.32 |
| Co—20Cr—35Ni—10Mo "MP35N" ASTM F 562 | 8.43 | 233 | 930 | 414 | 516 | 45 | 0.18 |
| Co—20Cr—16Ni—16Fe—7Mo "Phynox" ASTM F 1058 | 8.30 | 221 | 950 | 450 | 500 | 45 | 0.20 |
| TITANIUM ALLOYS | | | | | | | |
| CP Titanium ASTM F 67, Grade 1 | 4.50 | 107 | 300 | 200 | 100 | 30 | 0.19 |
| Ti—6Al—4V Alpha/beta ASTM F 136 | 4.43 | 105 | 860 | 795 | 65 | 10 | 0.72 |
| Ti—6Al—7Nb Alpha/beta ASTM F1295 | 4.74 | 106 | 1000 | 900 | 100 | 12 | 0.85 |
| Ti—15Mo Beta grade ASTM F2066 | 4.95 | 83 | 793 | 655 | 168 | 22 | 0.79 |
| REFRACTORY | | | | | | | |
| Tantalum | 16.60 | 185 | 207 | 138 | 69 | 25 | 0.06 |
| Niobium | 8.57 | 103 | 195 | 105 | 90 | 25 | 0.10 |
| Tungsten | 19.3 | 411 | 3126 | 3000 | 126 | 3 | 0.73 |
| Molybdenum | 10.2 | 324 | 1540 | 1386 | 154 | 15 | 0.43 |

TABLE 1-continued

Physical and mechanical properties of selected materials.

| | DENSITY gr/cm³ | ELASTIC MODULUS G Pa | ULTIMATE TENSILE STRENGTH MPa | 0.2% YIELD STRENGTH MPa | UTS-YIELD MPa | ELONG. % | ELASTIC RANGE % |
|---|---|---|---|---|---|---|---|
| PRECIOUS | | | | | | | |
| Pt—10Ir | 21.55 | 150 | 340 | 200 | 140 | 25 | 0.13 |
| NITINOL | | | | | | | |
| Martensitic | 6.45 | 40 | 1200 | 200-300 | 900-1000 | 25 | 1.9 |
| Cold worked 40% | 6.45 | 40 | 1450 | NS | NS | 12 | 4-6 |
| Superelastic | 6.45 | 90 | 1400 | NS | NS | 14 | 6-8 |
| MAGNESIUM | | | | | | | |
| Mg3Al—1Z | 1.8 | 45 | 255 | 162 | 93 | 10-25 | 0.36 |

In one embodiment, a support structure is provided having one or more cells defined by at least two sections, wherein one section is more pliable than another section. Each unit cell may be formed of at least two distinct, mechanically connected sections with different mechanical behaviors. One section acts as a relatively rigid support for the more flexible section. In certain configurations, the more flexible section is responsible for most, if not all, of the expansion of the stent. In some embodiments, a cell includes two interconnected sections of unequal dimensions. In one embodiment, a cell may include two struts having unequal thicknesses, widths, and/or cross sections. For example, a first strut may have a thickness less than the thickness of a second strut.

In some embodiments, a first strut of the cell is configured to be more flexible than a second strut of the cell. In certain embodiments, the first and second struts are each concave in shape in a collapsed configuration. In certain embodiments, the first strut has substantially the same shape as the second strut in a collapsed configuration. The more flexible or pliable first strut may be transitioned from a first stable collapsed position having a first distance from the second strut to a first stable expanded position having a second distance from the second strut, the second distance being greater than the first distance.

Based on the geometry of the struts, this transition of the first strut from the first stable collapsed position to a first stable expanded position requires the application of some amount of force until the first strut passes through a transition point, after which time the first strut may continue expanding to the stable expanded configuration position without any additional force being applied. Similarly, the first strut may move from the stable expanded configuration position to the stable collapsed position, requiring an amount of force required to reach a transition point, after which time the first strut continues to move to the collapsed configuration position without any additional force being applied.

Additional force may be applied to the structure in either the stable collapsed configuration or the stable expanded configuration to achieve additional and useful expanded and/or collapsed configurations. In certain embodiments, a unit cell in a stable collapsed configuration may be deformed to have a second stable collapsed configuration whereby the area of the unit cell is decreased. In particular embodiments, the structure is plastically deformed by crimping. Plastically deforming the unit cell to a plastically deformed collapsed configuration can occur with sufficient force to impart a desired reduced area of the unit cell. Such plastic deformation causes the medical device comprising the one or more unit cells to reach and substantially maintain a compressed geometry. In certain embodiments, the compressed geometry is suitable for delivery of the medical device within a body lumen. Likewise, one or more cells of the medical device may be plastically deformed beyond the original stable expanded configuration to a plastically deformed stable expanded configuration by the application of an outward force. Such plastic deformation causes the medical device comprising the one or more unit cells to reach and substantially maintain an expanded geometry.

In certain embodiments, plastic deformation of the first, more flexible strut is used to achieve plastically deformed stable configurations. For example, an amount of force sufficient to plastically deform the first strut may be applied when the first strut is in a collapsed position. Such force is typically applied at least in part in a direction toward the second less flexible strut. The plastically deformed first stmt attains a second collapsed or contracted position having a distance closer to the second strut. In some embodiment, the second, less flexible strut may also experience plastic deformation or geometrical variance with the deformation of the first strut.

Once plastic deformation has occurred to a plastically deformed collapsed configuration, the cell does not return to predetermined stable collapsed configuration. Likewise, once plastic deformation has occurred to a plastically deformed expanded configuration, the cell does not return to predetermined stable expanded configuration. Instead, the cell substantially maintains its collapsed or expanded configuration to which it was plastically deformed. It will be appreciated that the size and shape of the cell may be gradually decreased or increased by additional plastically deforming force, thereby allowing the stent to be collapsed or expanded through a continuum of diameters, perimeters, cross-sectional areas and/or sizes.

Certain embodiments include the unit cells described herein. In one embodiment, a one unit cell device may be used. For example, one unit cell lumen support may be used. In certain embodiments, unit cells of certain embodiments include one or more unit cells in a column, such column being arranged in a tubular structure. In certain embodiments, one or more columns may be connected together as further described herein. In certain embodiments, rings of the multistable unit cells having an inversion point between expanded and collapsed configurations, may be used together with convention unit cells that do not have the inversion geometry discussed herein. For example, one ring of enhanced unit cells (i.e., having an inversion point geometry) may be adjacent to a ring of conventional unit cells that do not posses such inversion point geometry.

Embodiments will now be described with reference to the drawings provided. Although embodiments will be discussed in connection with certain medical devices shown in the drawings, it is understood that such discussion is to facilitate an understanding of the preferred embodiments only, and is not intended to limit the scope of the present application to the embodiments shown in the figures.

As presently contemplated, one embodiment of a medical device having one or more cells is a stent. Alternatively, embodiments of the medical devices described herein could take the form of a multistable valve, an expander, a clip, a loop, a ring, or other like medical devices and/or lumen supports which use expandable cells. For the sake of simplicity, embodiments relating to stents are described below.

Figure 2:
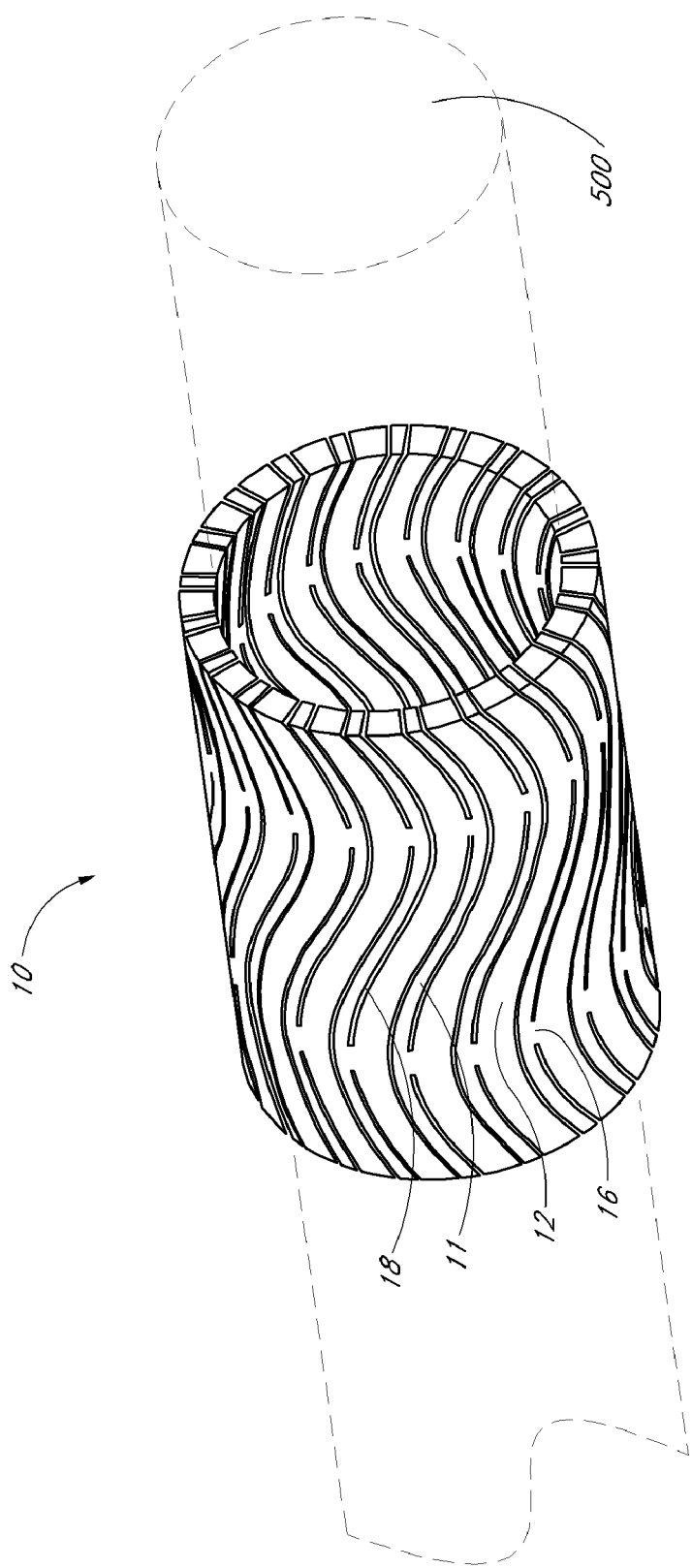
FIG. 2 is a supportive structure in a stable collapsed configuration in accordance with one embodiment.

Referring now to FIGS. 1 and 2, an embodiment of a supportive structure in the form of stent 10 is shown. Stent 10 includes a plurality of cells having at least bistable configurations described in greater detail in the Besselink patent. Stent 10 comprises a number of thick struts 12 interconnected to thin struts 14 by connector members 16. Thick struts 12 typically have different dimensions than thin struts 14. For example, thick struts 12 may have a greater thickness, width, or cross-section than thin strut 14. In a preferred embodiment in which the thicknesses of struts 12 and 14 are different, thick struts 12 are between about 1% to about 200% thicker than thin struts 14, although it will be appreciated that the strut thicknesses may be equal or may be different by some amount outside this range.

Stent 10 may comprise one or more materials. In particular embodiments, stent 10 comprises a material having a certain elastic range, elongation, and ultimate tensile strength as noted above. In some embodiments, stent 10 is at least partially formed of such a material. In some embodiments, stent 10 is fully formed of such a material. In some embodiments, thin struts 14 are partially or fully made of a cobalt-chromium alloy. In certain embodiments, thick struts 12 are partially or fully made of a cobalt-chromium alloy. Stent 10 may be formed of a uniform material or may be a combination of one or more materials. For example, some embodiments may include thin struts 14 formed of a first material and thick struts 12 formed of a second material.

The construction of stent 10 includes a series of elements with an arrangement of unit cells that enable stable expanded and stable collapsed configurations. There are several ways to manufacture a stent based upon this principle. In certain embodiments, an arrangement of wire or strips may be welded together at specific places. The particular pattern or arrangement can also be made in a flat plate and then welded, brazed or crimped to a more or less cylindrical shape or a cylindrical mid section with two conical ends with larger diameters. Another possibility is metal deposition in the desired pattern onto a substrate or the use of sintering of prealloyed powder. A further method is making the stent from a tubular shaped starting material, such as a hollow tube of cobalt-chromium alloy, with a pattern of slits or slots made in the wall by means of etching, grinding, cutting (e.g., with a laser, water, etc.), spark erosion or any other suitable method. In some embodiments, unit cells are manufactured in a collapsed configuration such that the loss of material due to cutting is reduced as compared to unit cells being formed in the expanded configuration. One of skill in the art will appreciate other methods of making the stents and other medical devices.

Thick struts 12 and thin struts 14 define openings 18 having an area. The size of openings 18 varies in response to the relative position of struts 12 and 14. In particular, as stent 10 transitions between an expanded configuration described in FIG. 1 to the collapsed configuration described in FIG. 2, the size of openings 18 decreases. Likewise, the outer diameter of stent 10, which is tubular with a circular cross-sectional profile, also decreases. Stent 10 may also be transitioned from the expanded configuration described in FIG. 1 to the collapsed configuration described in FIG. 2 by the application of force in a radially-inward direction. Such a transition is appropriate for coupling stent 10 to a delivery device. For example, stent 10 may be coupled onto a stent delivery device such as a balloon catheter. In certain embodiments, stent 10 is placed over a balloon catheter 500 and crimped into place over the balloon.

When stent 10 is transitioned to the collapsed configuration described in FIG. 2, thin struts 14 move from an expanded position to a collapsed position closer to thick struts 12. Movement of the thin struts 14 may be initiated by a radially inward force to stent 10. Thin struts 14 pass a critical point after which time thin struts 14 "snap" to the stable collapsed position closer to thick struts 12 without additional external force. Likewise, stent 10 may be transitioned to the expanded configuration described in FIG. 1. Movement of thin struts 14 may be initiated by a radially outward force being applied to stent 10, such as a radial outward force from a balloon catheter. After application of an amount of sufficient force to reach a transition point at which force is reduced and the thin struts 14 "snap" to the expanded position without additional application of outward force. Materials having desired elasticities, such as the cobalt-chromium alloy, undergo this "snapping" into place and resist recoil when further expanded from the stable expanded state or further compressed from the stable collapsed state.

As shown, stent 10 may be coupled to a balloon catheter 500. In certain embodiments, the stent 10 is delivered to the balloon catheter 500 in a stable expanded configuration. Application of a compression force to stent 10 may result in the balloon catheter 500 collapsing through the transition point where no further force is required for the stent 10 to assume the stable collapsed configuration. In certain embodiments, the balloon catheter 500 has a diameter greater than the diameter of the stent 10 in the stable collapsed configuration. In such embodiments, the stent 10 may grip the balloon catheter 500 because it exerts an elastic force (in the inward direction toward the stable collapsed configuration) on the balloon catheter. In certain embodiments, as further discussed herein, stent 10 may be plastically deformed by a compressing force, such that the stent 10 assumes a smaller diameter than in its stable collapsed configuration.

In certain embodiments, stent 10, or other medical devices having unit cells described herein, may be configured to have a plurality of collapsed and expanded configurations. For example, stent 10 may include two or more types of unit cells. In some embodiments, the two or more types of unit cells may require different amounts of forces for transitioning the cell from the first stable position to the second stable position. For example, a stent 10 may have a first unit cell type and a second unit cell type. Each cell type may include a thick strut and a thin strut. However, the thin struts may have different thicknesses and require different amounts of force to transition the thin strut from the collapsed position to the expanded position, or vice versa. In particular embodiments, the diameter of a multi-stable medical device may be adjusted through a series of stepwise configurations. Accordingly, the device may be well suited for supporting a variety of passageways.

Figure 3A:
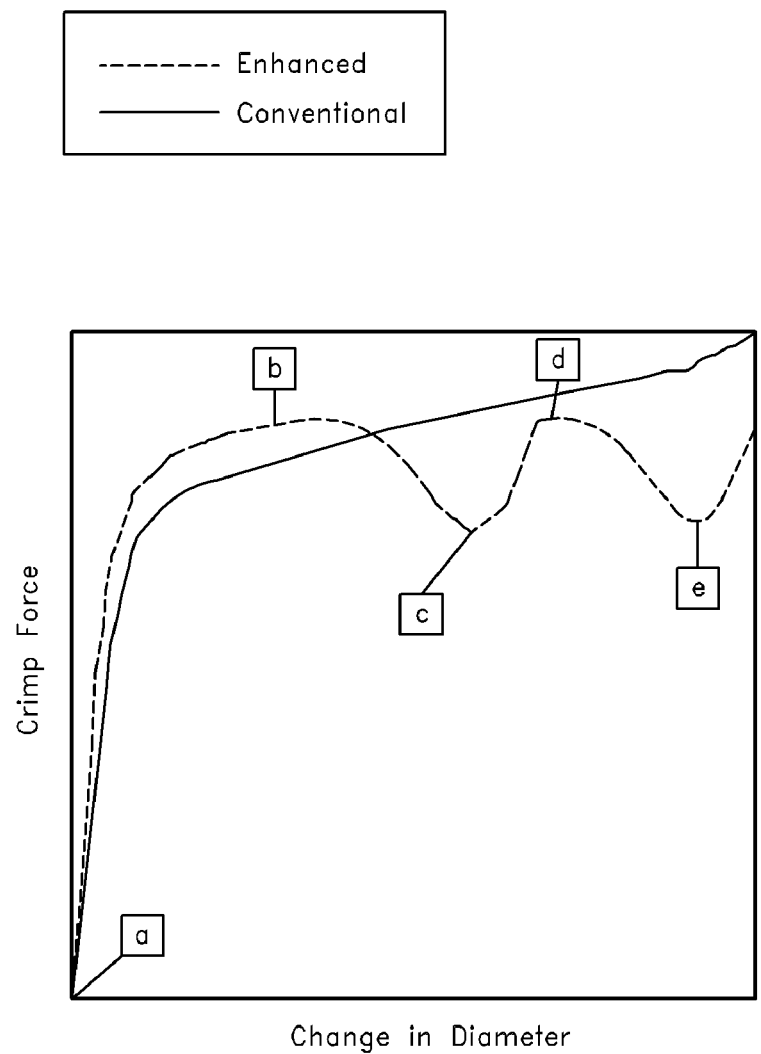
FIG. 3A is graph comparing the crimp force to the reduction in diameter between a stent constructed in accordance with one embodiment and another stent of a known design.
Figure 3B:
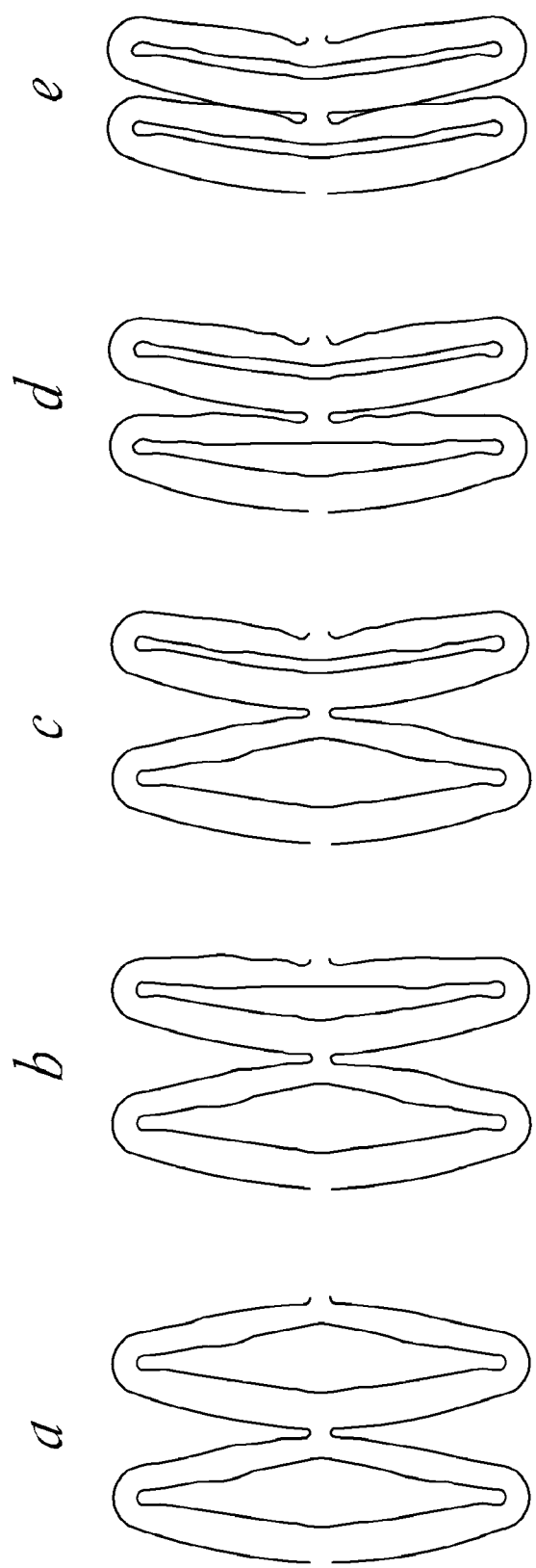
FIG. 3B is a drawing of various unit cell configurations as correlated to points on the graph of FIG. 3A

FIG. 3A shows the amount of crimping or collapsing force on the two unit cells shown in FIG. 3B. As shown in FIG. 3A, the enhanced line shows crimping force versus diameter (mm). The conventional plot represents a unit cell of a conventional balloon expandable stent. In the (a) configuration shown in FIG. 3B, the unit cells begin from a stable expanded configuration. While the enhanced plot of FIG. 3A represents a crimp force being applied to the cells in the stable expanded configuration, it is also contemplated that a crimp force could also be applied from a plastically deformed expanded configuration or a stable collapsed configuration.

Upon application of a crimping force to the unit cells in the (a) configuration, one unit cell begins to collapse. When sufficient force has been applied to reach the inversion point (denoted as (b) in FIG. 3A) of one of the unit cells, one unit cell has a reduced area as shown on configuration (b) of FIG. 3B. It is at this point that the thin strut of the unit cell moves to the collapsed position without application of additional force.

After collapsing unit cell through inversion point (b), the cell continues to close to the configuration shown in configuration (c) of FIG. 3B upon application of the crimp force. The crimp force is decreased as the strut transitions from configuration (b) to configuration (c). At point (c) in FIG. 3A, the first unit cell has passed through the inversion point and has reached a stable collapsed configuration as shown in configuration (c) of FIG. 3B.

The second unit cell may also pass through an inversion point upon application of a crimping force. Point (d) of FIG. 3A shows the amount of force required to reach the inversion point of the second unit cell. At this point, the two unit cell embodiments adopt configuration (d) of FIG. 3B, which represents the geometry at which the cell may transition to the collapsed position without application of additional force.

As the second unit cell passes through the transition point, it snaps closed to configuration (e). This configuration is represented as point (e) in FIG. 3A. In this configuration, the unit cell may elastically oppose an amount of force that is less than the force required to transition the cell back to the stable expanded configuration or the amount of force required to plastically deform the cell to a plastically deformed collapsed configuration.

It should be noted that the force required to collapse a support structure that has a plurality of rows of different types of cells may behave in a similar manner. It also should be note that the diameter and application of force may vary depending on the exact construction of the unit cells of the medical device. The conventional designation of FIG. 3A shows the amount of force required to crimp a conventional balloon expandable stent. Since the unit cells of such stents do not have structures and geometries like those described herein, the unit cells do not pass through the same types of inversion points (points of decreasing force).

Figure 3C:
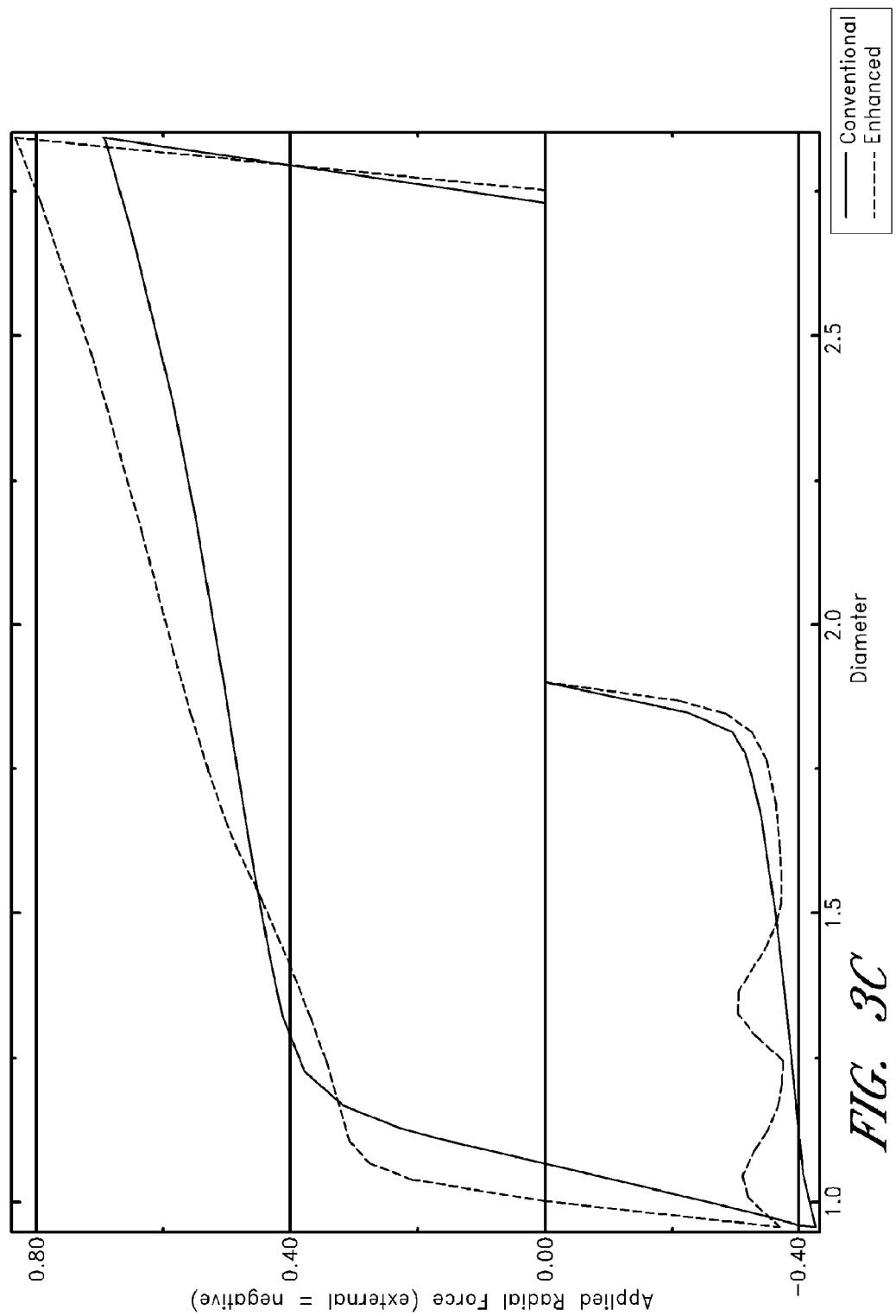
FIG. 3C is a graph which shows crimping of unit cells shown in FIG. 3B as well as expansion through an inversion point to a plastically deformed configuration.

Referring to FIG. 3C, the designated enhanced plot shows the applied force versus diameter curves for a stent comprising two unit cell types as shown in FIG. 3B. The device having the two cells types in the stable expanded configuration has an initial diameter of about 1.8 mm. The device may then be crimped. This external force to the device is represented as a negative force in the graph. As demonstrated in FIG. 3A and discussed above, the first unit cell type passes through a first inversion point where the applied external force is reduced. The first cell then passes through to a stable collapsed state, wherein the stent has a first diameter of about 1.3 mm. The second unit cell may pass through a second inversion point where the applied external force is reduced. The second unit cell then passes through to a stable collapsed state, such that the stent has a smaller diameter of about 1.1 mm. This type of behavior may be seen with stents having two cell types which require different amounts of forces to collapse the various cell types. In certain embodiments, this type of behavior may be observed when different portions of a stent are collapsed.

As can further be seen in FIG. 3C, additional external force is applied to crimp the enhanced stent. Such external force plastically deforms the stent to a reduced diameter. Upon ceasing the external force, the stent comprising the two unit cells type recoils. Notably, such recoil is less than the conventional balloon expandable stent shown in the conventional plot in FIG. 3C. As can be seen in the conventional plot, a conventional balloon expandable stent may be crimped from a starting diameter of 1.8 mm to the same minimum diameter as the enhanced stent. However, upon ceasing the force to the conventional balloon expandable stent, the stent recoils to a diameter greater than that of the enhanced stent.

Application of outward radial force to the enhanced stent in the crimped configuration results in elastic expansion of the stent. Such force may be delivered to the stent by a balloon. As shown in the graph, the stent undergoes elastic and plastic expansion as this outward radial force is applied. At about 0.3 units of force, the enhanced stent reaches an inversion point where one or more cell types of the stent pass through the inversion point. Thus, the amount of applied radial force decreases. Such decrease in radial force may be seen as a small valley between 1.2 and 1.3 mm. As the enhanced stent is expanded through this stable expanded configuration, applied force is continually in an elastic and plastic regime through the stable expanded configuration. In comparison, the conventional plastically deformable stent experience no such release of energy as it does not have inversion point geometry. Thus, no valley is seen for the conventional stent.

The enhanced stent is then further expanded into a plastic regime. Application of a force capable of deforming the stent increases the stent diameter to about 2.8 mm. Upon removal of the force, the stent recoils to a diameter of about 2.75 mm. As compared to the conventional stent, the enhanced stent demonstrates reduced recoil, resulting in a larger diameter plastically deformed expanded configuration.

FIGS. 4-6A depict a section of a supportive structure that is displayed in a flattened profile. This section 22 of device 20 may be obtained by severing a row of connector members 24 and unrolling section 22 from a tubular shape into a flat shape. While certain embodiments are described herein in terms of a flattened profile of a tubular structure, it is understood that flattened profiles may also be shown of devices not having a tubular structure. Thick strut 26 is connected to thin strut 28 by connector members 24. Openings 30 are defined by thick strut 26 and thin strut 28.

Figure 4:
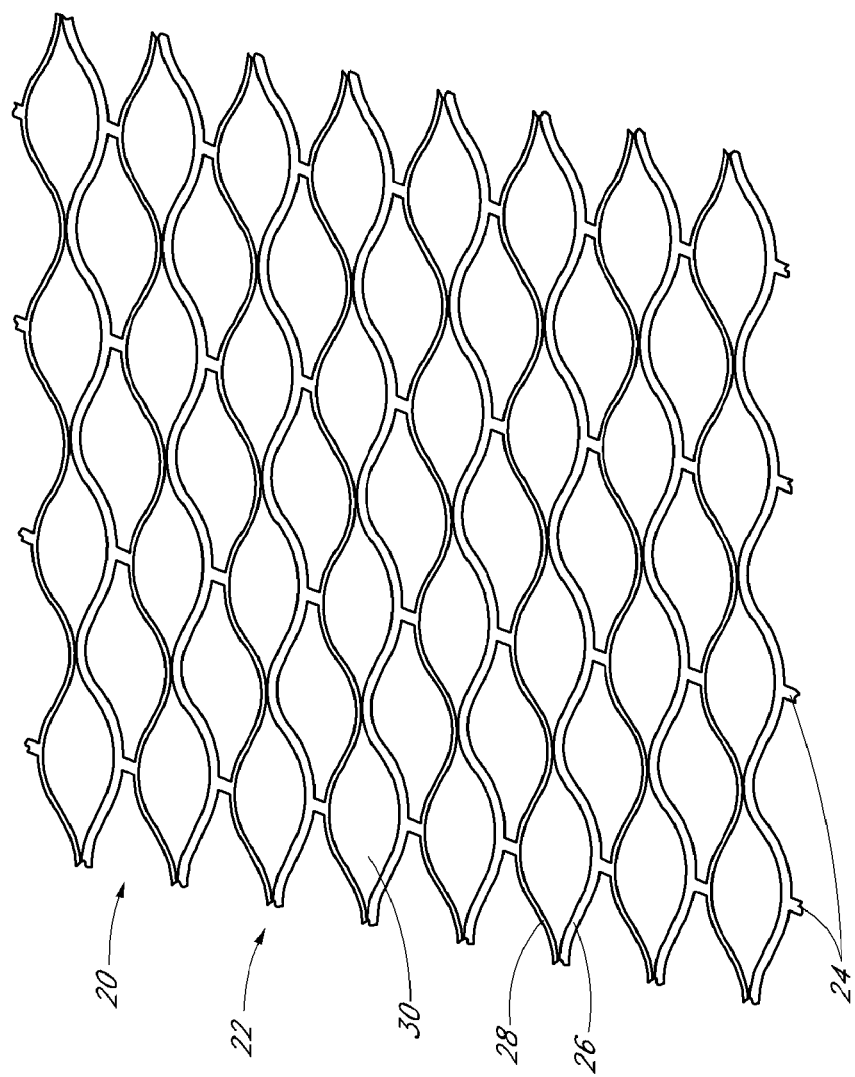
FIG. 4 is a section of a support structure in a first stable expanded configuration that is displayed in a flattened profile in accordance with one embodiment.

FIG. 4 depicts section 22 with thick strut 26 and thin strut 28 in a first predetermined stable expanded configuration. In some embodiments, this configuration may be appropriate for positioning device 20 over a delivery device prior to crimping, as further described herein. While device 20 has a predetermined expanded diameter, the diameter of device 20 may be further expanded upon plastic deformation of the unit cells.

Figure 5:
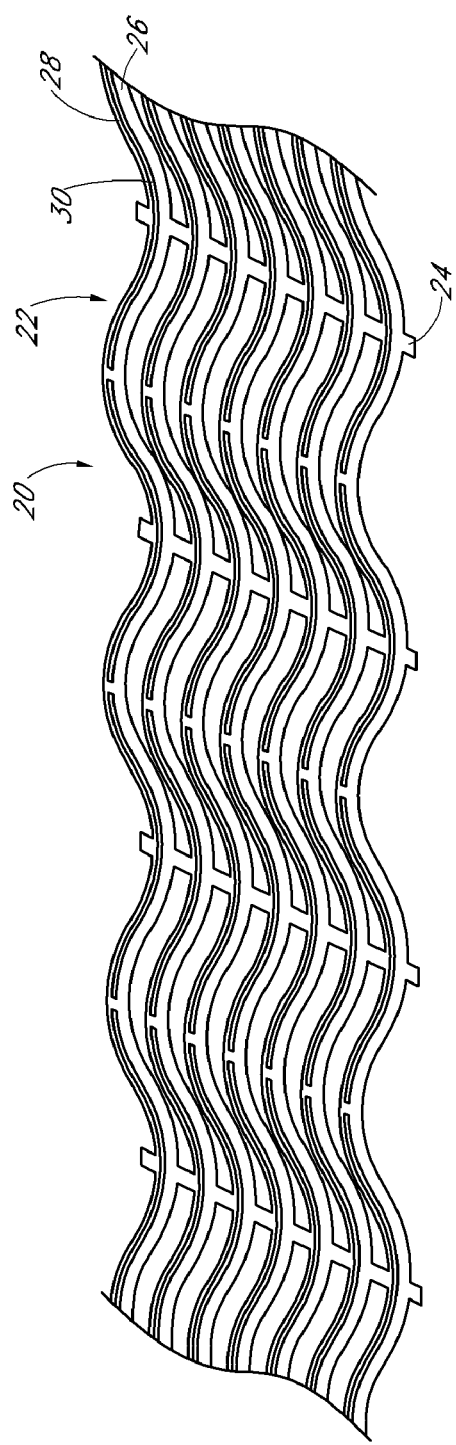
FIG. 5 is a section of a supportive structure in a first stable collapsed configuration that is displayed in a flattened profile in accordance with one embodiment.
Figure 6A:
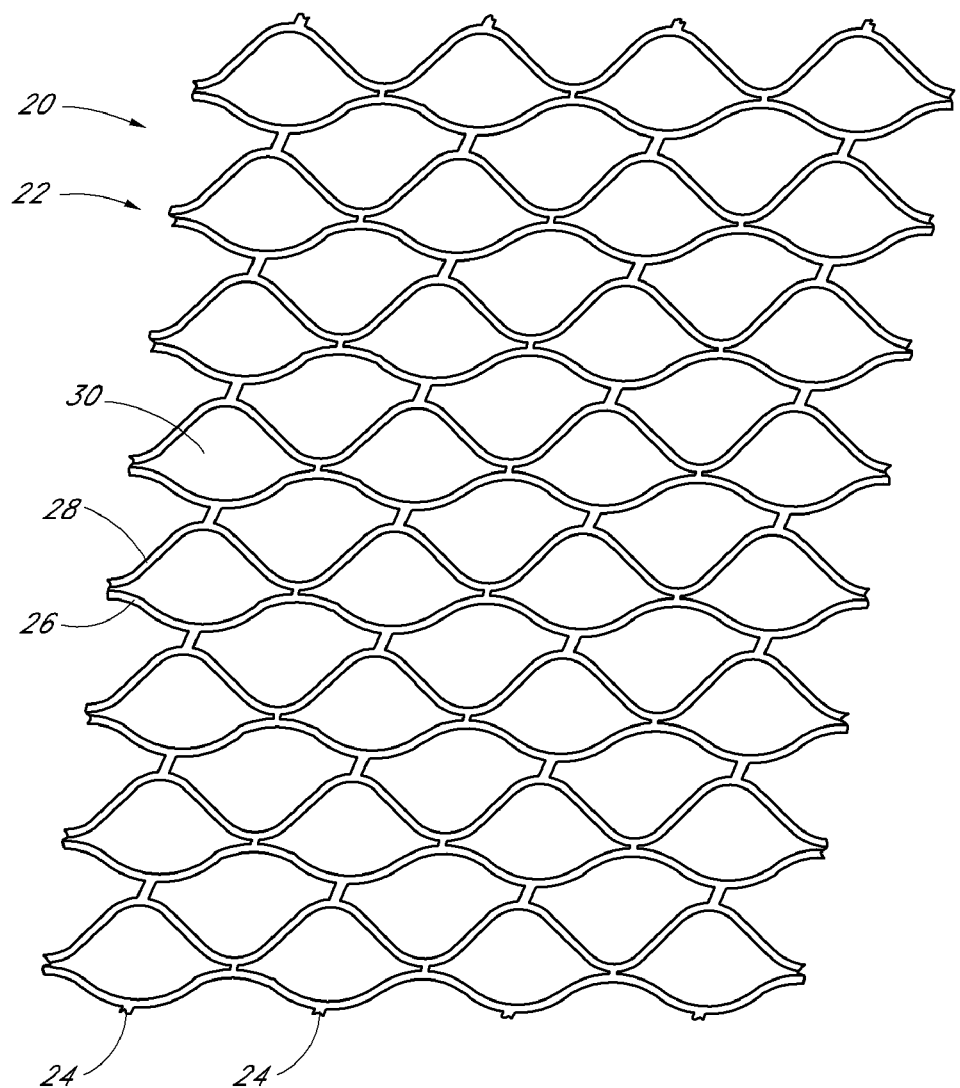
FIG. 6A is a section of a supportive structure in a plastically deformed expanded configuration that is displayed in a flattened profile in accordance with one embodiment.

FIG. 5 depicts section 22 having a first predetermined stable collapsed configuration. In this configuration, thin strut 28 has been transitioned to a stable position toward the corresponding thick strut 26 of the unit cell opening 30. This collapsed configuration may be obtained by applying a radial inward force to device 20 in an expanded configuration. For example, device 20 having an expanded configuration as shown in FIG. 4 may be transitioned to the collapsed configuration by applying a compressive force, e.g., crimping. Likewise, device 20 may be expanded from the collapsed configuration as shown in FIG. 5 to the expanded configuration as shown in FIG. 6A by the application of a radial outward force to device 20.

Advantageously, certain embodiments of devices, such as the device shown in FIGS. 5 and 6, may include plastically deformable unit cells. As such, one or more unit cells of device 20 may be capable of assuming a plurality of plastically deformed configurations, whether these configurations are plastically deformed collapsed configurations or plastically deformed expanded configurations.

In some embodiments, it may be desirable to plastically deform device 20 to an expanded configuration wherein the device has a greater diameter than the expanded configuration shown in FIG. 4. FIG. 6A describes unit cells of section 22 of device 20 after plastic deformation has occurred. In this embodiment, thin struts 28 have been plastically deformed away from thick struts 26. Plastic deformation may reduce the recoil that may otherwise occur when a material is elastically displaced. Moreover, plastic deformation of the cells may alter their characteristics, so that the cells no longer tend to "snap" back to a predetermined stable expanded configuration.

In certain embodiments, device 20 may be configured to obtain a plastically deformed diameter selected from a continual range of diameters larger than the diameter of the predetermined stable expanded configuration. The one or more unit cells of device 20 may be expanded from the predetermined stable expanded configuration to a plastically deformed expanded configuration. To accomplish this, an outward radial force may be applied to device 20. Such force may be greater than the total elastic strain limit of the portion of the unit cells being plastically deformed. Once the elastic strain limit is reached, the plastically deformed unit cell may continue to be expanded and deformed in response to a radially-outward force resulting in a larger diameter of device 20. This diameter may be increased to any plastically deformed diameter along a continuum as desired within the range of structural integrity of device 20. Such plastic deformation can occur without limitation to a select number of step-wise diameters.

Figure 6B:
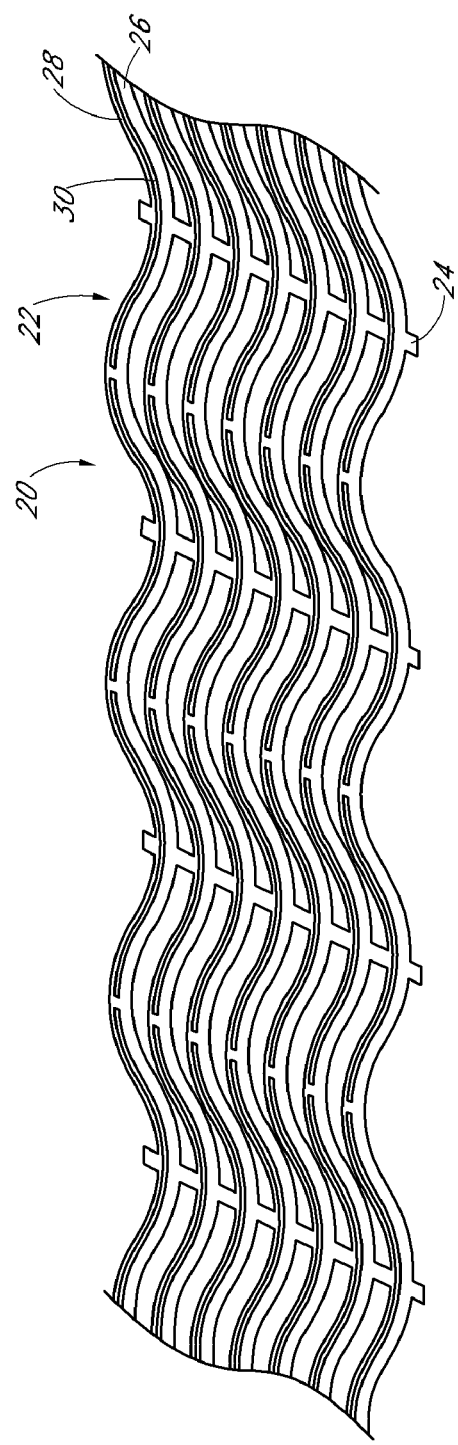
FIG. 6B is a section of a supportive structure is a plastically deformed collapsed configuration that is displayed in a flattened profile in accordance with one embodiment.

In certain embodiments, device 20 may be configured to obtain a plastically deformed diameter selected from a continual range of diameter less than the diameter of the predetermined stable collapsed configuration. With reference to FIG. 6B, device 20 is shown in a plastically deformed collapsed configuration. To achieve such plastically deformed collapsed configuration, an inward radial force may be applied device 20 in the predetermined stable collapsed configuration, as shown in FIG. 4. Such inward force should be greater than the elastic strain limit of the portion of the unit cell being plastically deformed. Once the elastic strain limit is reached, the plastically deformed unit cell may continue to be collapsed and deformed in response to radial inward force resulting in a smaller diameter of device 20.

Figure 7:
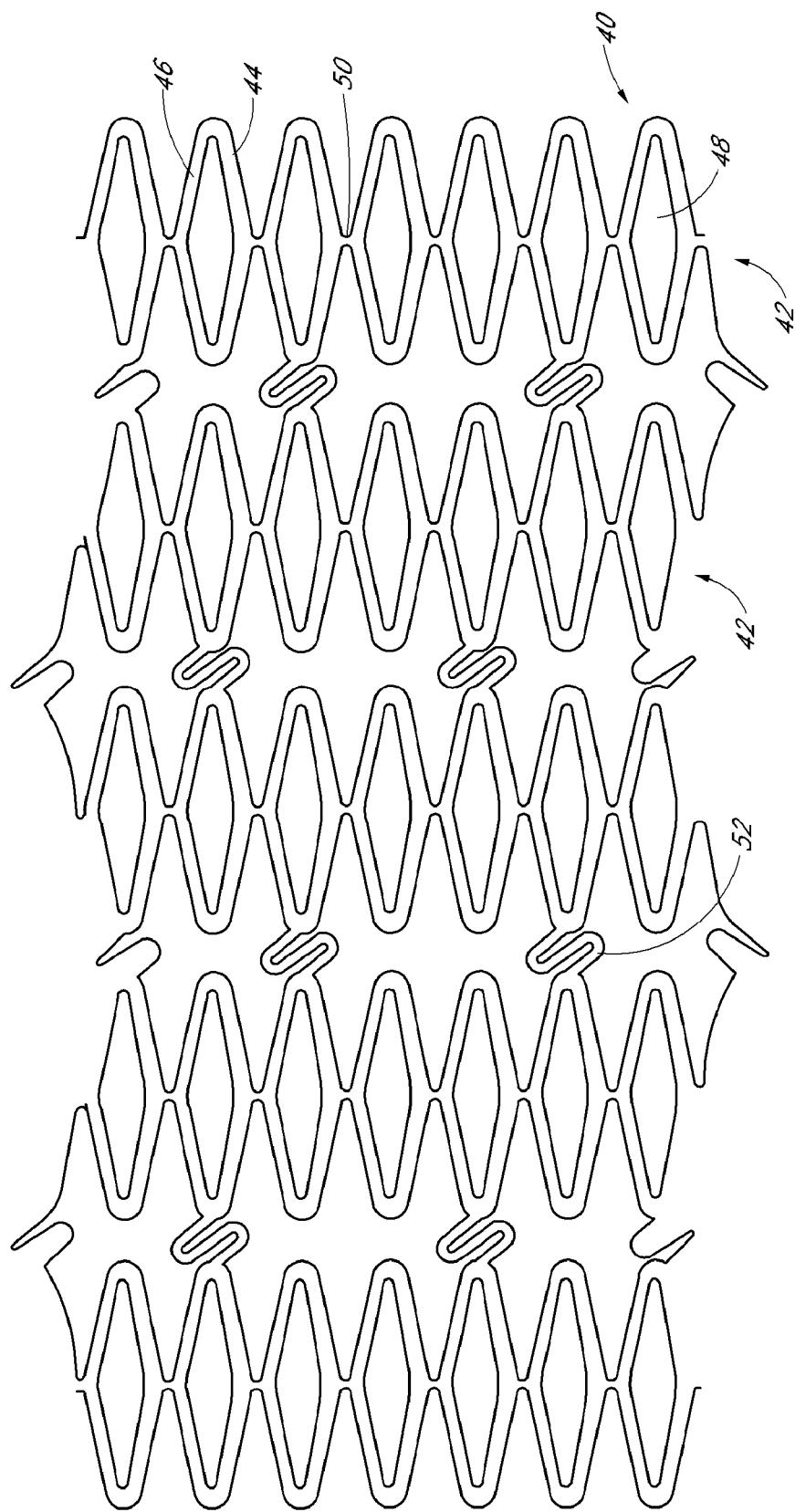
FIG. 7 is a section of a supportive structure that is displayed in a flattened profile in accordance with one embodiment.
Figure 8:
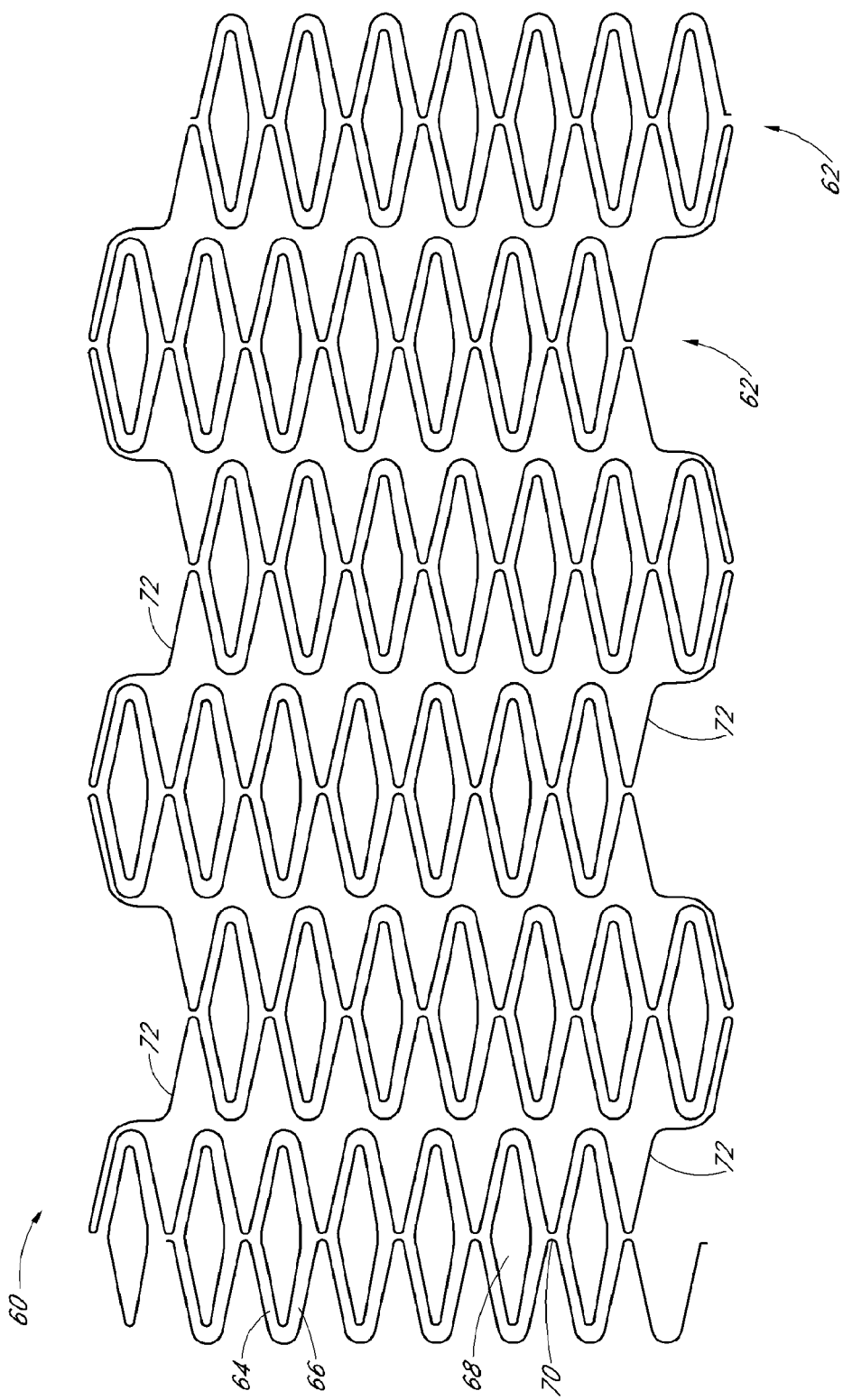
FIG. 8 is a section of a supportive structure that is displayed in a flattened profile in accordance with one embodiment.
Figure 9:
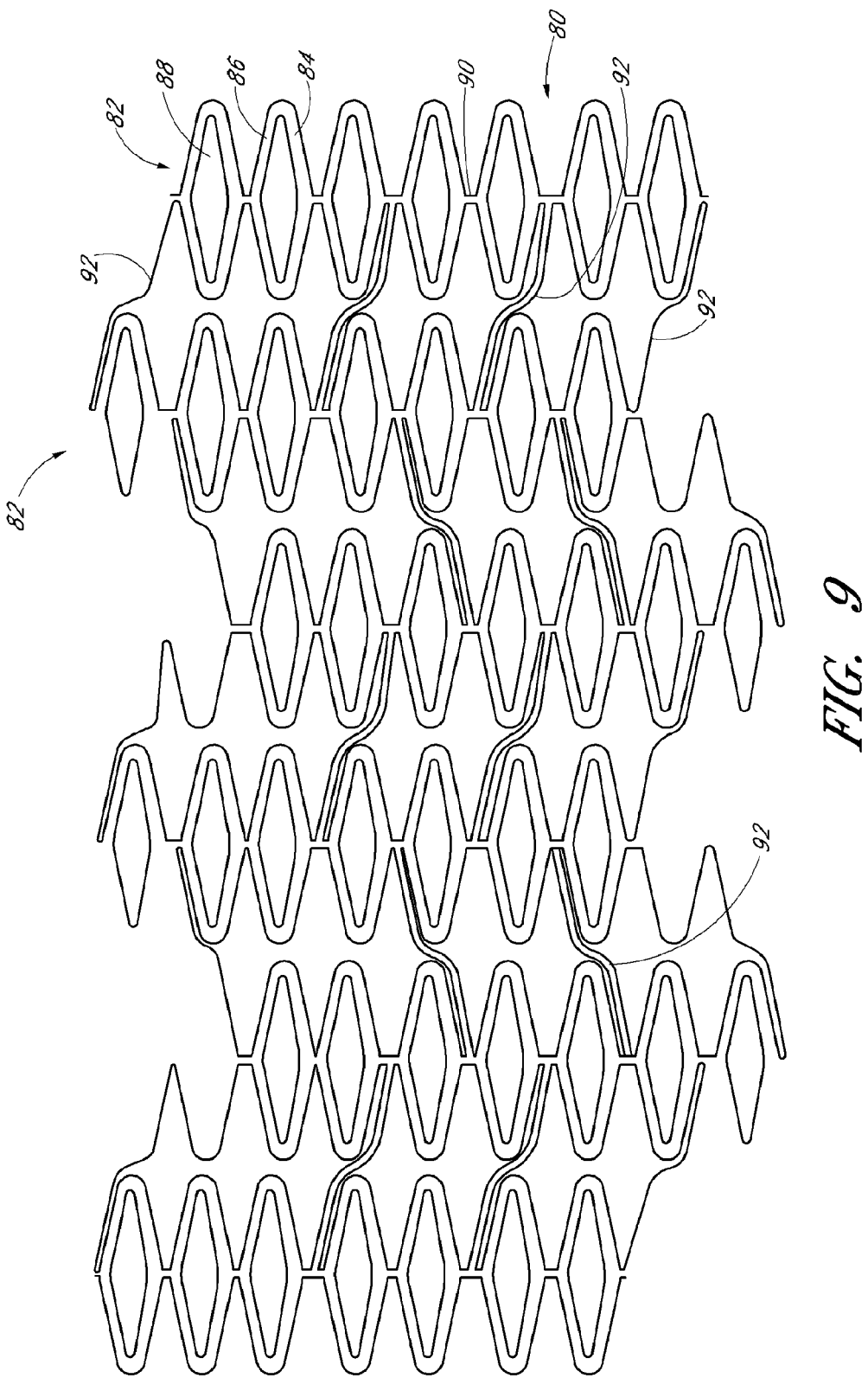
FIG. 9 is a section of a supportive structure that is displayed in a flattened profile in accordance with one embodiment.

FIGS. 7-9 demonstrate other flat profiles of supportive structures in accordance with certain embodiments. FIG. 7 depicts supportive structure 40 having five columns 42 of cells (columns may also be referred to as rings). Thick struts 44 and thin struts 46 define openings 48 and are connected by articulations 50.

In some embodiments, articulations 50 are configured to provide spacing between thick struts 44 and thin struts 46. In certain embodiments, such spacing provides certain advantageous properties to the unit cell. In some embodiments, the spacing is configured to provide flexibility to the cell when in a collapsed or an expanded configuration. As such, the spacing may be configured such that one or more unit cells adapt to curvatures, relief, or other particular architecture of the lumen passageway when collapsed or expanded. In certain embodiments, the articulations may be configured to geometrically change the amount of force required to reach the inversion point of the cell.

Adjacent columns 42 of unit cells may be connected by row interconnectors 52. Interconnectors 52 allow adjacent columns 42 to be displaced relative to one another. Interconnectors 52 are S-shaped bent connect bars having at least one peak and one trough. In certain embodiments, interconnectors 52 may have two or more bends. Interconnectors 52 connect adjacent cells which are substantially lateral to each other. Interconnector 52 may be spaced apart by a distance from other interconnects in same axis by one or more unit cells. As shown, interconnectors 52 are spaced apart by two unit cells. In certain embodiments, interconnectors 52 have substantially the same thickness as the thick strut 44 or the thin strut 46. In certain embodiments, interconnectors 52 have a thickness less than thick strut 44 or thin strut 46. In certain embodiment, thickness or pliability of interconnector 52 may be varied such that the supportive structure 40 is adapted to conform to the deployment lumen. In certain embodiments, interconnectors 52 are configured for better nesting of the supportive structure 40 in a collapsed or crimped configuration.

In certain embodiments, articulations 50 and interconnectors 52 provide supportive structure 40 with the ability to adapt to certain lumen architectures. In some embodiments, the combination of the articulations 50 and interconnectors 52 provide spacing between unit cells such that one or more unit cells of device 40 may be displaced relative to its manufactured, crimped, or deployed position. Off-axis displacement of a unit cell relative to the longitudinal axis of the tubular supportive structure 40 unit cell may be obtained within ranges of flexibility of the articulations 50 and interconnectors 52.

FIG. 8 depicts supportive structure 60 having six columns 62 of cells. Thick struts 64 and thin struts 66 define openings 68 and are connected by articulations 70. Column interconnectors 72 connect adjacent columns 62, and allow adjacent columns 62 to be displaced relative to one another. As shown, an interconnector 72 extends between an articulation 52 of one cell to an articulation of another cell in an adjacent column 62. Interconnector 72 extends along thin strut 62 and bends to a direction substantially parallel to the axis of a column 62 of cells. Interconnector 72 extends in the substantially parallel direction between adjacent columns 62 in the axis of the columns 62. Interconnector 72 bends to extend along the thick strut and joins articulation 70 of a cell in an adjacent row. As shown, interconnector joins laterally displaced unit cells. In certain embodiments, the displacement between interconnected unit cells may be varied depending on the application.

FIG. 9 depicts supportive structure 80 having six columns 82 of cells. Thick struts 84 and thin struts 86 define openings 88 and are connected by articulations 90. In some embodiments, articulations 90 have a length which is approximately equal to half the distance between the apices of thin strut 86 and thick struts 84 of the same unit cell. In some embodiments, the length (in the axis of the columns) of the articulation can be about 5 to about 50 percent of the distance between the apices of the thin and thick struts of the same unit cell. In certain embodiments, articulations 90 may have varying lengths. In the embodiment shown, adjacent column interconnectors 92 extend between articulations 90. In such articulations, the distance may be increased to accommodate the thickness of interconnectors 92. Interconnectors 92 extend from articulation 90 of a unit cell in a column 82 of unit cells to an articulation 90 in an adjacent row. In this embodiment, interconnector 92 has a similar shape to the interconnectors shown in FIG. 8. However, interconnector 72 joins adjacent cells which displaced to a lesser degree than that shown in FIG. 8.

In certain embodiments, unit cells may be configured such that the thick struts and thin struts are arranged in a repeating pattern that is consistent throughout the supportive structure. In certain embodiments, the pattern may vary within the same column or different columns of unit cells. For example, two adjacent unit cells within the same column may be arranged such that the thick struts of each cell are adjacent and are connected through joints or articulations. Such a pattern may repeat such that the thin struts are also adjacent to other thin struts and are connected to each other by articulations. In certain embodiments, such a pattern may repeat throughout the structural support or within certain columns. In one embodiment, adjacent columns may oppositely arranged unit cells (e.g., thick struts on top in the first column and thick struts on bottom in the second, adjacent column, relative to a planar arrangement).

While FIGS. 7-10 show certain types of cells structures, cell interconnectors, and articulations, many different types of these are known in the art and may be used. In certain embodiments, other types of cell structures using principles described herein may be used. In certain embodiments, various types of cell interconnectors may be used including, but not limited to valley to valley interconnectors, side to side interconnectors, valley to side interconnectors, peak to side interconnectors, or peak to peak connectors may be used in some embodiments. In certain embodiments, interconnectors may have various thickness and configurations. In certain embodiments, spacing between interconnectors may vary depending on the application. Moreover, described in FIGS. 7-10 are various features of structural supports. It is intended that one or more of these features may be incorporated into any embodiment described herein.

Figure 10A:
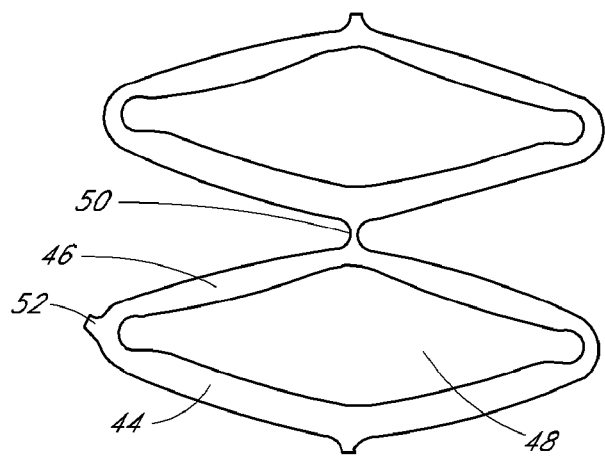
FIGS. 10A-10E depict two cells from the embodiment of FIG. 7 in a flattened profile and in variety of configuration in accordance with one embodiment.

FIGS. 10A-10E depict two exemplar cells of the device 40 in a flattened profile. FIGS. 11A-11E depict a single column 42 of unit cells of device 40 arranged in a tubular structure. In one embodiment, device 40 is formed such that openings 48 are spaced as described in FIGS. 10A and 11A. As such, thick struts 44 are separated from thin struts 46 and device 40 may be configured to have a predetermined stable collapsed configuration and an expanded configuration. As shown in FIGS. 10A & 11A, the unit cells are shown in the expanded configuration.

Device 40 or a similar device may be coupled to a suitable delivery device. For example, if the delivery device is a balloon catheter, device 40 may be placed around the balloon catheter in the vicinity of the balloon. Device 40 may then be transitioned toward the collapsed state by crimping or otherwise applying a radially-inward directed force. In some applications, it may be desirable to collapse device 40 to the fully collapsed position. In other applications it may be desirable to prevent the contraction of device 40 to the fully collapsed state by interaction with the delivery device. In such embodiments, the outer diameter of the delivery device may be greater than the diameter of the device in the stable collapsed configuration, but smaller than a diameter where the force is reduced during compression or contraction of the device, as discussed above. As such, the device 40 would apply an inward force on the delivery device, e.g., on the balloon catheter.

Figure 10B:
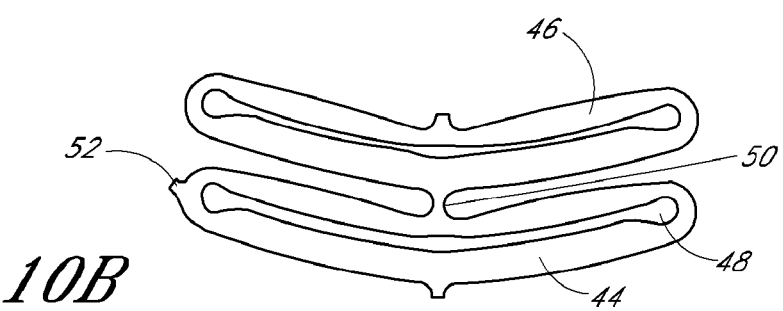
Figure 10C:
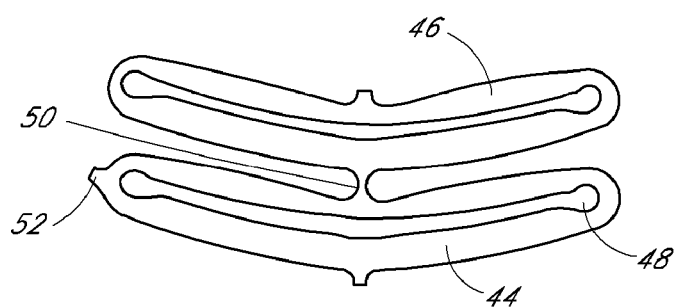
Figure 11A:
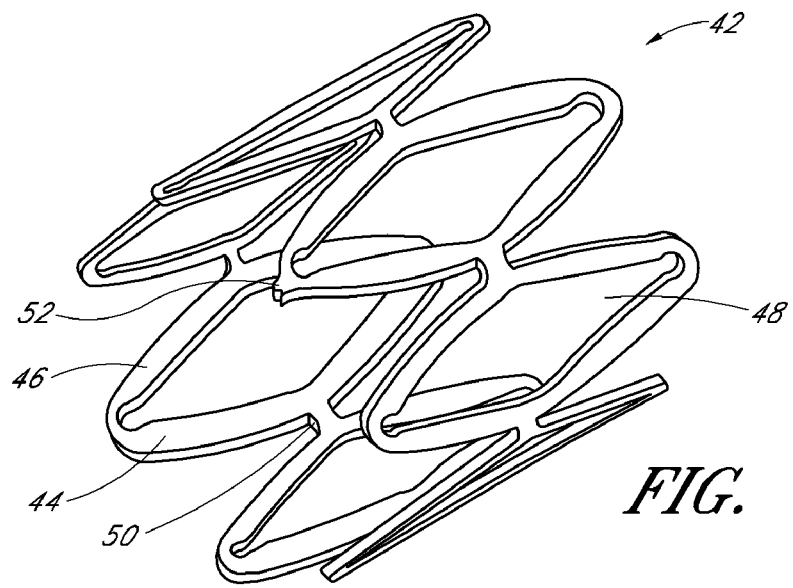
FIGS. 11A-11E depict a column of cells from the embodiment of FIG. 7 in a variety of configurations in accordance with one embodiment.
Figure 11B:
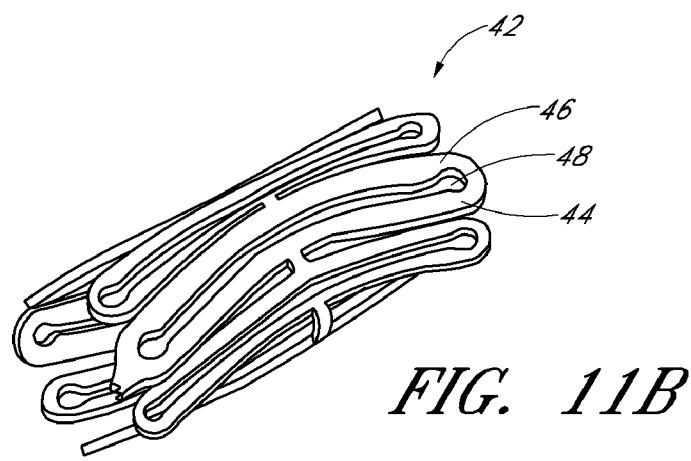
Figure 11C:
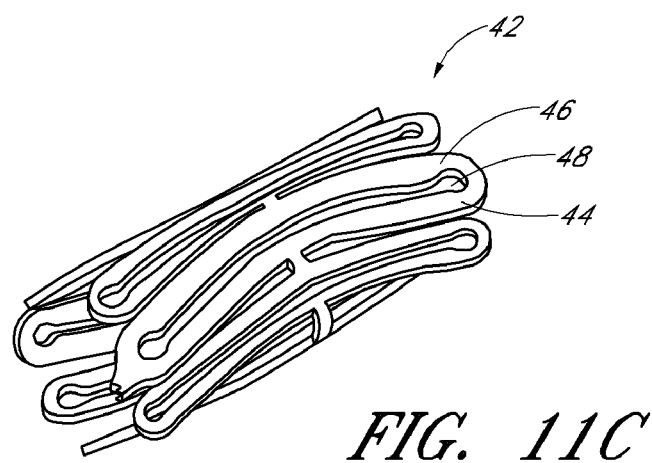

FIGS. 10B and 11B depict the respective portions of device 40 after crimping to a desired diameter. Such configuration is achieved by applying a radially inward force to device 40 sufficient to transition the one or more cells of the device from the stable expanded configuration to the stable collapsed configuration and sufficient to plastically deform the unit cell to a plastically deformed collapsed configuration. However, recoil of stent may result in an increased diameter which is shown in FIGS. 10C and 11C. However, such recoil is less than that which may occur when crimping of other plastically deformable designs formed of similar materials.

Referring to FIGS. 10C and 11C, device 40 may be plastically deformed to a collapsed diameter less than the predetermined stable collapsed diameter. A radially inward force may be applied to the device 40 in the predetermined stable collapsed configuration. Such force must be sufficient to plastically deform the unit cell.

Figure 10D:
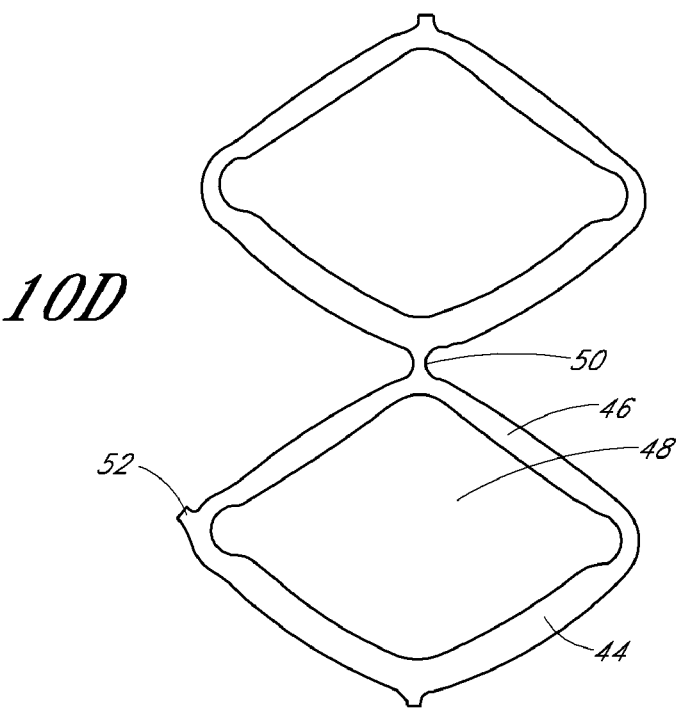
Figure 10E:
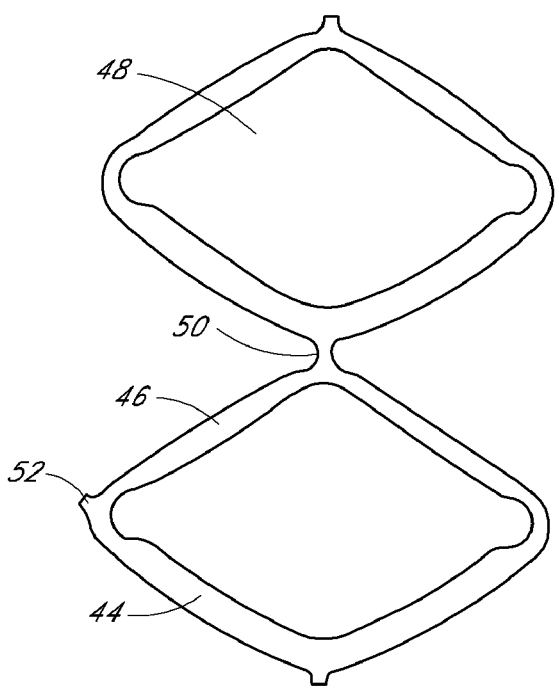
Figure 11D:
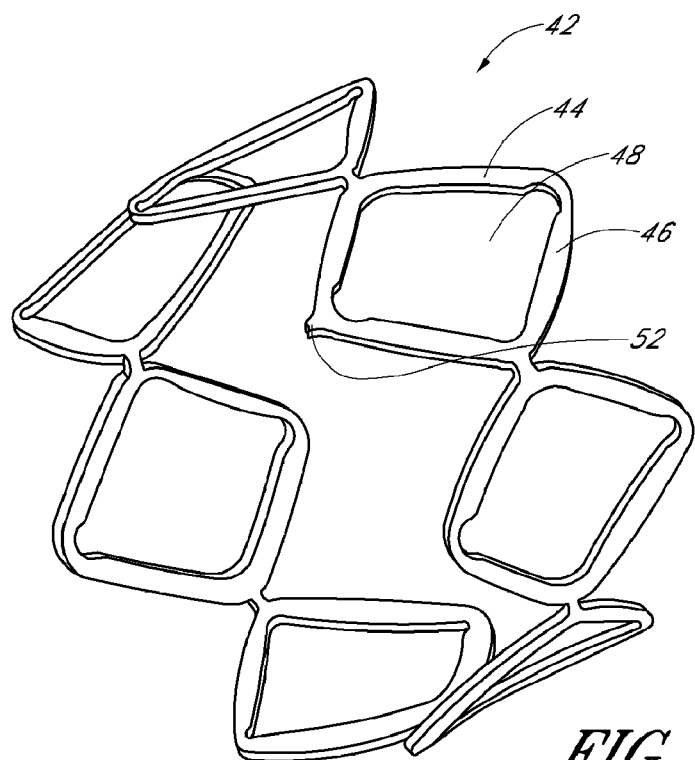

Referring to FIGS. 10D and 11D, device 40 is shown in an expanded configuration achieved by applying sufficient radial outward force to plastically deform the device from the predetermined stable expanded configuration. As the outward force is increased, device 40 may undergo expansion and may then begin to plastically deform. As the difference in the sizes between thick struts 44 and thin struts 46 is increased, a similar difference may be seen in the amount of plastic deformation between those two components. While the device 40 in this configuration may incur some recoil resulting in the plastically deformed expanded configuration shown in FIGS. 10E and 11E, the amount of recoil is less than that of conventional balloon expandable supporting structures or those structures which use a non-preferred material (e.g., highly elastic material).

Figure 11E:
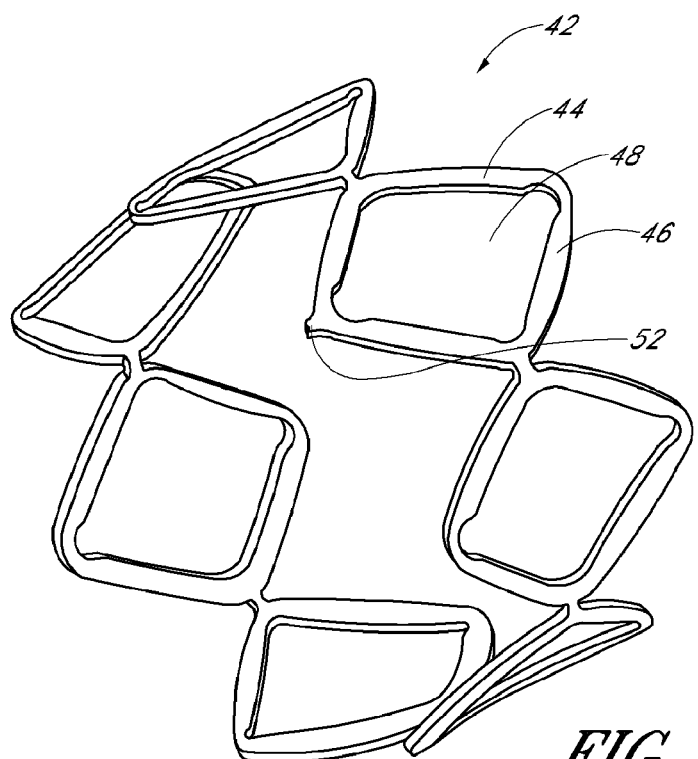

While there are various states of plastically deformed expansion, one example in the continuum of deformation is described in FIGS. 10E and 11E. It will be appreciated that device 40 need not be deformed to this degree, or alternatively, may be deformed further to result in a still larger outer diameter. Because device 40 is expanded plastically, its diameter need not be limited to discrete predetermined dimensions.

Figure 12A:
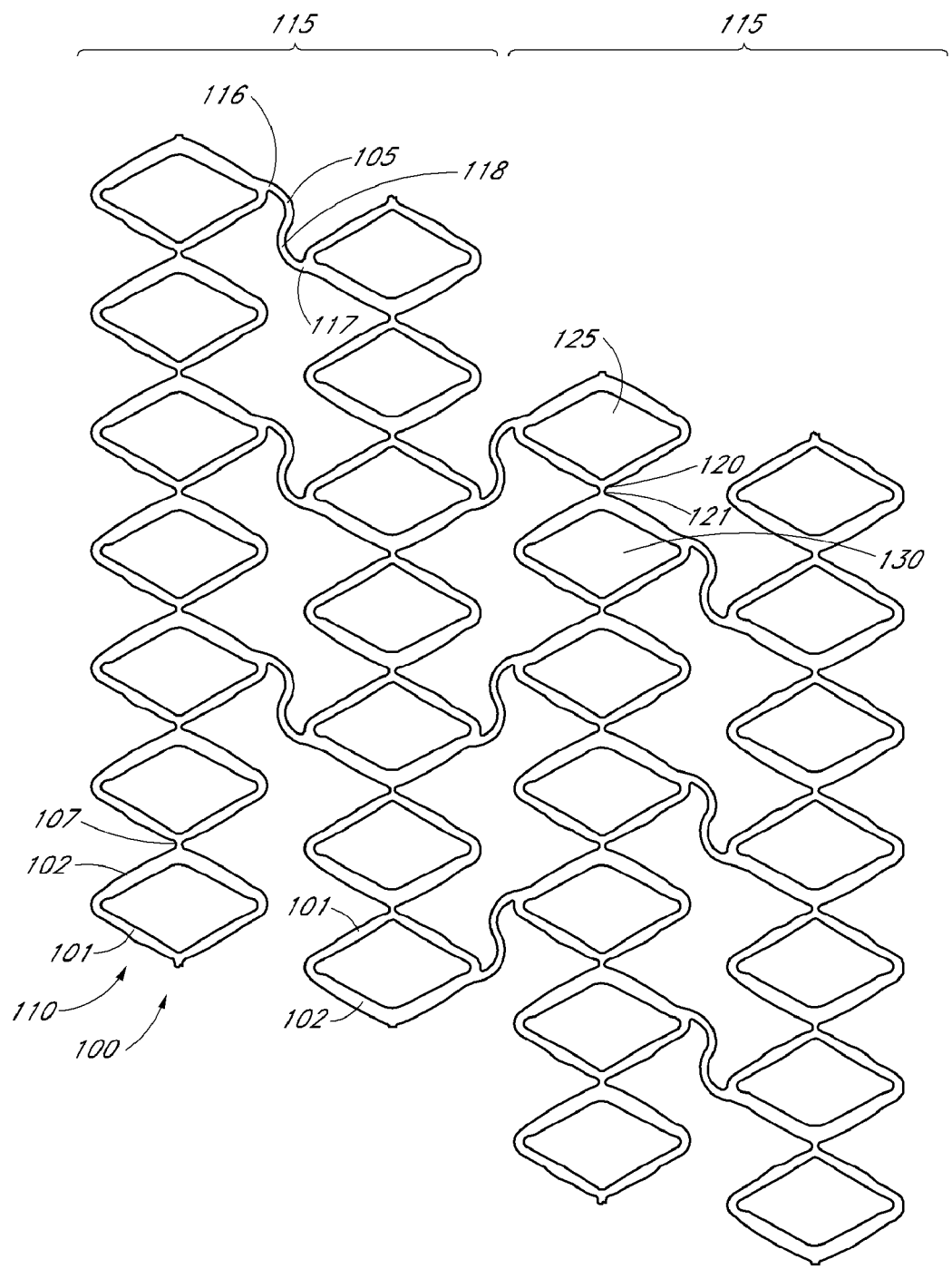
FIGS. 12A-12B depict one embodiment of a supportive structure according to one embodiment in an expanded and a collapsed configuration.
Figure 12B:
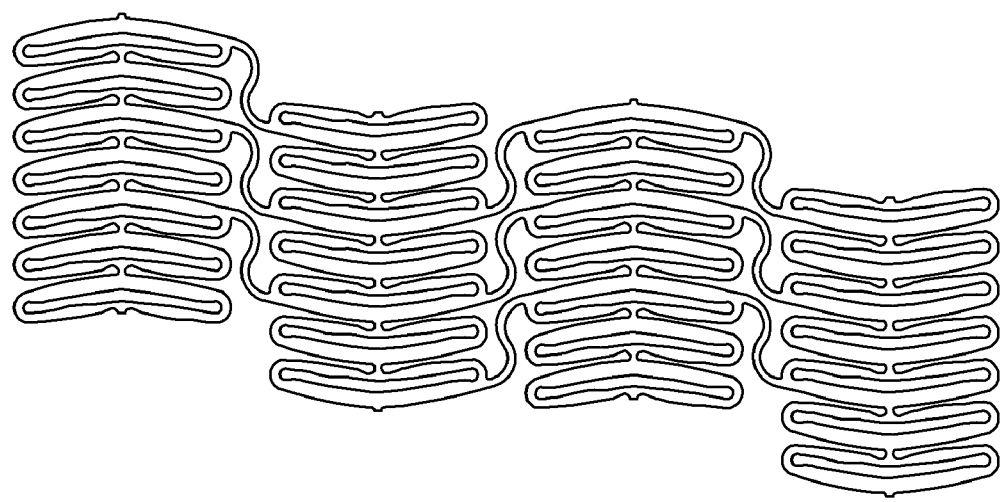

FIGS. 12A and 12B show one embodiment of a unit cell 110 incorporated into a portion of a medical device. The portion of the medical device includes a repeating pattern 115. The medical device incorporating the unit cell 110 can be a stent or other lumen support or other medical device as discussed herein. Although the unit cell 110 is incorporated into a repeating pattern, it can be used in structures that do not repeat in a regular manner. In this embodiment, the repeating pattern 115 includes a plurality of unit cells 110 arranged in a plurality of rows of and in a plurality of columns.

The orientation and position of the unit cells 110 can be varied from row to row, within a row, from column to column, or between columns. In the illustrated embodiment, the unit cells of adjacent rows are arranged in opposite directions. In particular, a row 100 is arranged in a manner so that a thick strut 102 of a first unit cell in the row 100 is on the top and a thin strut 101 is on the bottom. In an adjacent row 105, the thick strut 102 of a second unit cell in the adjacent row 105 is on the bottom and a thin strut 101 is on the top. "Top" and "bottom" as used in this paragraph is relative to the unit cells as shown in FIG. 12A. This alternating configuration of unit cells in adjacent rows assists in nesting of the device when in its collapsed configuration in some embodiments.

The repeating pattern 115 also includes a plurality of interconnectors 105 that interconnect different rows of the pattern. For example, in the illustrated embodiment, the interconnect 105 connects the adjacent rows 100 and 105. As with other interconnects discussed herein, the interconnect 105 can extend from a peak of a unit cell of one embodiment.

The interconnector 105 can have any suitable geometry and configuration. For example, the interconnector 105 can have a first end 116 configured to couple with a first row and a second end 117 configured to couple with a second row. In some embodiments, the interconnector 105 has an elongate portion 118 between the first and second ends 116, 117 that is selected to enhance a performance characteristic of the pattern 115. For example, FIG. 12B illustrates that the elongate portion 118 is shaped so that the first and second ends 116, 117 extend away from lateral side of unit cell to which they are coupled, e.g., generally perpendicular to a longitudinal axis of the rows in which the unit cells are located and so that the elongate portion extends generally parallel to the longitudinal axis of the rows in which the unit cells are located. This arrangement provides for a more compact geometry at least in an unexpanded state.

The length of the interconnect 105, e.g. of the elongate portion 118 thereof, can be selected to enhance a performance characteristic of the pattern 115. For example, the interconnect 105 can be configured to couple peaks of unit cells that are adjacent to each other in the collapsed state. Alternatively, the interconnect 105 can be configured to couple peaks of unit cells that separated by at least one intervening peak in the adjacent row when the pattern 115 is in an unexpanded state. In the illustrated embodiment, each interconnect 105 connects peaks of unit cells in adjacent rows that are separated by at least one intervening unit cell in the collapsed state. FIG. 12A shows that the pattern 115 permits the adjacent rows to shift such that no intervening peaks separate the peaks to which the interconnect 105 is connected.

In some embodiments, interconnect 105 has a sinusoidal geometry. However, the interconnect 105 may also have other geometries described herein. In one embodiment, the interconnect 105 is spaced apart from adjacent interconnects such that the interconnects do not contact each other when in the collapsed configuration, shown in FIG. 12B.

As discussed above, each unit cell also preferably is coupled to an adjacent unit cell along each row by an articulation 107. As discussed in more detail herein, articulations 107 enhance the plastic deformability of the unit cells, e.g., from a stable collapsed state to a crimped state, wherein the device or structure has a reduced diameter. In some embodiments, the articulations 107 mechanically isolate adjacent unit cells so that the adjacent unit cells are less rigid and are able to be plastically deformed to a greater extent than if the unit cells were directly coupled together. The articulations 107 can also enable the unit cells to plastically deform under a lesser force or pressure to the same extent than would be needed to expand unit cells that were directly coupled together.

The articulations 107 can take any suitable configuration. For example, in one embodiment, the articulation 107 includes a first end 120 that is coupled with a first unit cell 125 and a second end 121 that is coupled with a second unit cell 130. The connection between the articulation 107 and the unit cells 125, 130 can be at any suitable location, for example, at adjacent valleys of the two cells. In one arrangement, the articulation connects a thin strut of one unit cell with a thick strut of an adjacent unit cell. In some embodiments, the articulation 107 has a length between the ends 120, 121 that can be varied based upon a desired characteristic. For example, it may be desirable to elongate the articulation 107 to provide greater mechanical isolation between adjacent cells. On the other hand shortening the articulation 107 would provide a more compact arrangement. The articulation 107 is at least at long as the thickness of the thin strut 101 in one embodiment. In another embodiment, the articulation 50 is at least at long as the thickness of the thick strut 102.

Figure 13:
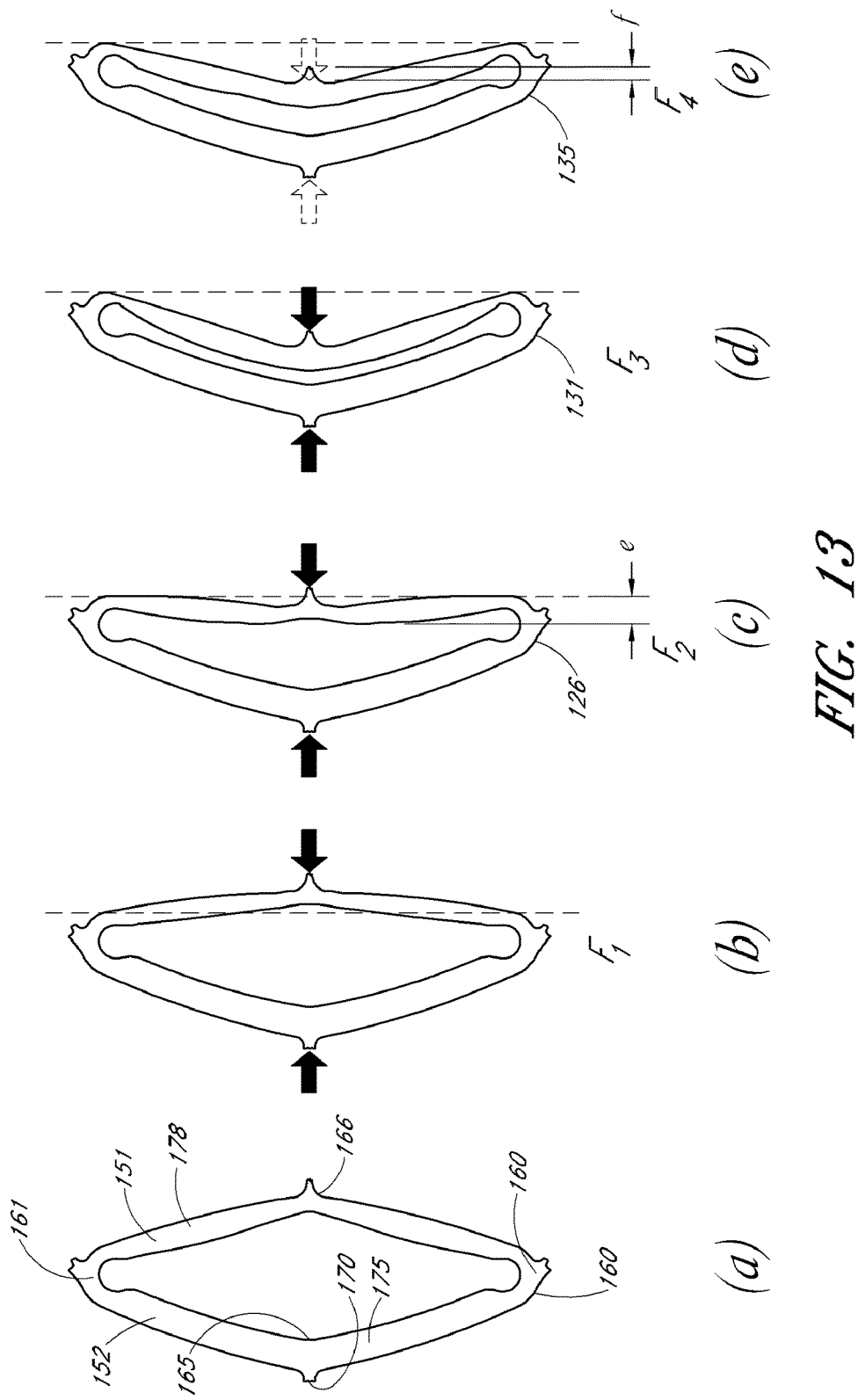
FIG. 13 is a schematic drawing of a process of crimping a unit cell from a stable expanded configuration through a stable collapsed configuration to a plastically deformed collapsed configuration.

FIG. 13 shows a unit cell 150 undergoing a crimping process.

In FIG. 13(a), the unit cell 150 is in a stable expanded configuration. The unit cell 150 is similar to those hereinbefore described and the descriptions of those cells are applicable to the unit cell 150. In particular, the unit cell 150 has a thin strut 151 and a thick strut 152. The thick and thin struts 152, 151 can be configured as elongated members extending between first and second ends 160, 161. The first ends 160 can be coupled together and the second ends at apices 165, 166. The apices 165, 166 are described elsewhere herein as "peaks" of the unit cell 150.

The apices 165, 166 can take any suitable form. In one embodiment, the apices 165, 166 have a portion which has localized thinning. In certain embodiments, such thinning is configured to promote flexibility of the thin strut from a collapsed position to an expanded position. As such, the apices may be used to control force required to reach the inversion point between the thick strut 152 and thin strut 151. In certain embodiments, the elongate member 175 of thick strut 152 may have varying thickness near apices 165. In certain embodiment, the elongate member 175 of thick strut 152 has a thickness that ranges between about 150 to about 200 percent compared to that of the apex 166 of the thin strut 151.

In some embodiments, the unit cell 150 is configured to couple to other unit cells, for example to form a repeating pattern suitable for forming all or a portion of a stent or other lumen supporting medical device. In one embodiment, an articulation 170 is located along the length of the elongate member 175 of the thick strut 152. In one embodiment, an articulation 170 is located along the length of the elongate member 178 of the thin strut 151. In one embodiment, the unit cell is configured such that at least in one expanded configuration the elongate member 175, 178 of at least one of the thick strut 152 and the thin strut 151 have a concave shape. In one arrangement, both of the thin strut 151 and the thick strut 152 have a concave shape such that the unit cell 150 has a diamond shape in at least one expanded configuration, as shown in FIG. 13(a).

FIG. 13(b) illustrates that application of an inward force (e.g., a radially inwardly applied force) on the unit cell 150 causing the thin strut 151 to move toward the thick strut 152. $F_1$ represents an amount of force that unit cell 150 elastically opposes. Such amount of force may be applied, however, cessation of the force would result in the cell expanding to the expanded position shown in FIG. 13(a). This causes the distance between the thick strut 152 and the thin strut 151 to be decreased at least at a location spaced from the apices 166, 165, and causes the unit cell to be compressed through the inversion point to a predetermined stable collapsed configuration 125.

FIG. 13(*c*) further illustrates an inversion point configuration 126 of unit cell 150. The designation e shows the elastic regime from the inversion point to the predetermined stable collapsed configuration. Each unit cell 150 is configured to have an inversion configuration 126. Such configuration 126 is a configuration in which the unit cell may move between stable collapsed and expanded configurations without the application of addition force. The inversion point configuration 126 is a configuration at which a force suddenly decreases to complete the transition to the collapsed or expanded configuration. In certain embodiments, described herein the inversion point geometry is used to minimize recoil in materials that would otherwise recoil beyond an acceptable range. $F_2$ represents a sufficient amount of force to transition the unit cell 150 from the stable expanded position shown in FIG. 13(*a*) to the inversion point at which no additional force is required to complete the transition from the expanded position to a collapsed position. Thus, $F_2$ is greater than $F_1$.

FIG. 13(*d*) shows that further application of an inward force to unit cell 150. Such inward force plastically deforms the stent. $F_3$ represents a plastically deformable amount of force. Such amount of force must exceed the elastic strain limit of the thin strut. In certain embodiments, $F_3$ is be greater than the force used to reach the inversion point $F_2$, but this depends on the exact configuration of the strut segments. In certain embodiments, articulation 170 may be configuration to have a shape which allows plastic deformation of the unit cell 150 to configuration 131

FIG. 13(*e*) illustrates the effect of recoil on the collapsed state of the unit cell 150. Once a sufficient amount of crimping force, $F_4$, has been applied to unit cell 150, the thin strut 151 elastically recoils. Thus, designation f represents this amount of elastic recoil, which can be measured as a distance. Thus, the unit cell transitions from the fully deformed state 131 to the free state 135 in which it has a plastically deformed collapsed configuration.

Figure 14A:
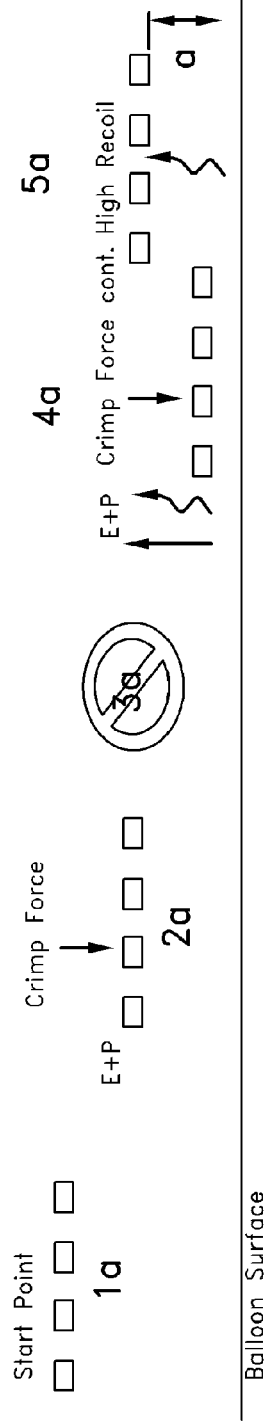
FIGS. 14A-14B are schematic drawings comparing a conventional crimping process for a stent to the crimping process for the improved stent.

Referring to FIG. 14A, a schematic drawing represents a conventional balloon expandable stent without desired geometries which allow the stent to pass through an inversion point. As such, the conventional balloon expandable stents has a high degree of recoil. Such stents are plastically deformable through a series of configurations (1*a*), (2*a*) and to the collapsed diameter (4*a*). However, such stents demonstrate a high degree of recoil denoted as a.

Figure 14B:
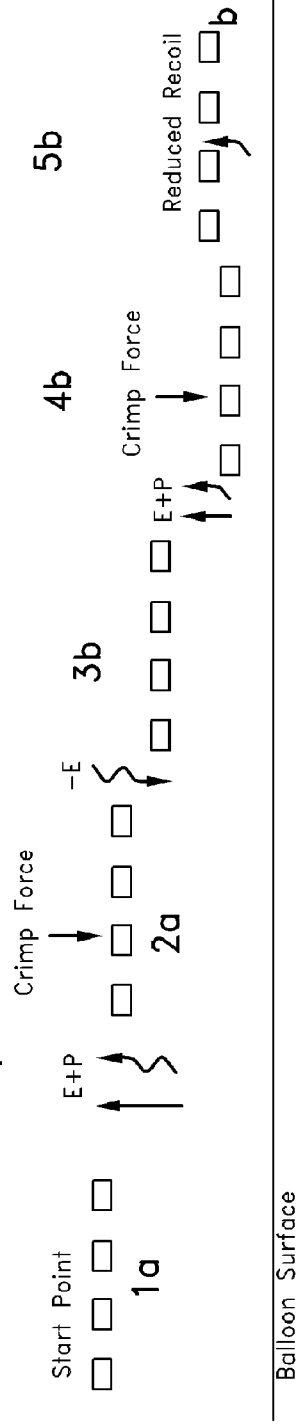

Referring to FIG. 14B, a balloon expandable stent having the geometries discussed herein and made of certain elastic materials may pass through a series of expanded configurations (1*b*) and (2*b*) and through an inversion point to reach configuration (3*b*) (also designated as the predetermined stable collapsed configuration). Upon application of a plastically deformable crimp force and then release, the stent exhibits reduced recoil when compared to the regular balloon expandable stent of FIG. 15.

Figure 15:
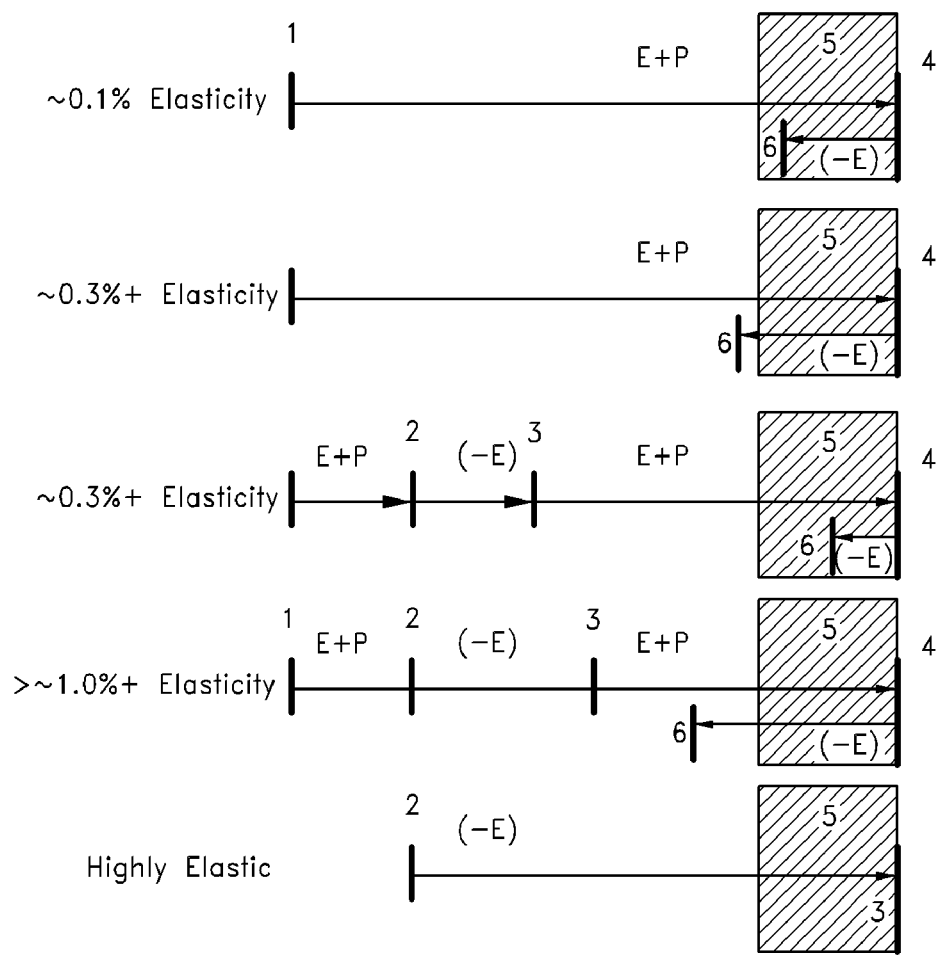
FIG. 15 is a schematic drawing comparing recoil of plastically and elastically expanded stents.

FIG. 15 shows a comparison of a conventional balloon expandable stents made of certain materials compared to stents having bistable geometries that have an inversion point and which are capable of undergoing plastic deformation. As discussed above, the material and the geometry of the stent contributes to reduced recoil when compared to other stents made of different materials or having different geometries. Stents made of materials having different elastic ranges are shown.

Referring to FIG. 15(*a*), stainless steel conventional balloon expandable stents expand by means of elastic and plastic deformation (E+P) from collapsed diameter (1) to desired expanded diameter (4). However, this is followed by elastic recoil (−E) to a diameter (6) within an acceptable range (5) that will provide good clinical outcomes. In particular embodiments, described herein, this acceptable range (5) is about 10% of the expanded diameter of the stent. As shown, this stainless steel type stents recoil within an accepted range, which has led to the common use of this type of stent.

Referring to FIG. 15(*b*), a convention Cobalt-x-y alloy stent is shown, such as stent made of L605 or MP35N. The elastic recoil (−E) from expanded diameter (4) is greater, approximately twice that of stainless steel shown in FIG. 15(*a*). Such recoil is outside of the accepted range of recoil, leading to a smaller stable diameter (6) that could lead to less desirable clinical outcomes. This can only be overcome by expanding this stent beyond expanded diameter (4), so that a clinically acceptable recoil diameter is achieved. However, that type of expansion requires higher pressures in the case of balloon expansion during angioplasty, and greater diameter expansion. Such conditions may damage tissue at the edges of the stent.

FIG. 15(*c*) shows one embodiment of the invention described herein. Such a stent may be made with materials such as a cobalt alloy, such as L605 or MP35N. During expansion, the stent passes from predetermined stable collapsed configuration (2) to predetermined expanded configuration (3) through an inversion point in which elasticity is reversed and released by the stent. Thus, less elastic recoil potential is built up during further deformation from predetermined stable expanded configuration (3) to plastically deformed expanded configuration (4). Hence, the stent recoils to diameter (6). As shown, the recoil is less than that experienced by example (a) or (b). Less elastic recoil provides a wider lumen passageway, which is known to provide better clinical outcomes. Such geometry overcomes one of the disadvantages generally associated with higher elastic alloys, namely elastic recoil outside of an acceptable range.

Referring to FIG. 15(*c*), an elastic range exceeding preferred values results in recoil beyond an acceptable range of recoil, even when the stent geometry allows the stent to pass through the inversion point between a predetermined stable collapsed configuration (2) and a predetermined stable expanded configuration (3).

FIG. 15(*e*) illustrates a highly elastic stent, such as one that uses Nitinol or other materials with greater than 1% and up to about 8% or higher elastic range. As diagramed here, such stents expand only by elastic energy from (2) to (3), with (3) being the final dimension and can be achieved to similar diameters as shown by position (4). However, such stents lack beneficial radial strength and radiopacity properties.

Figure 16:
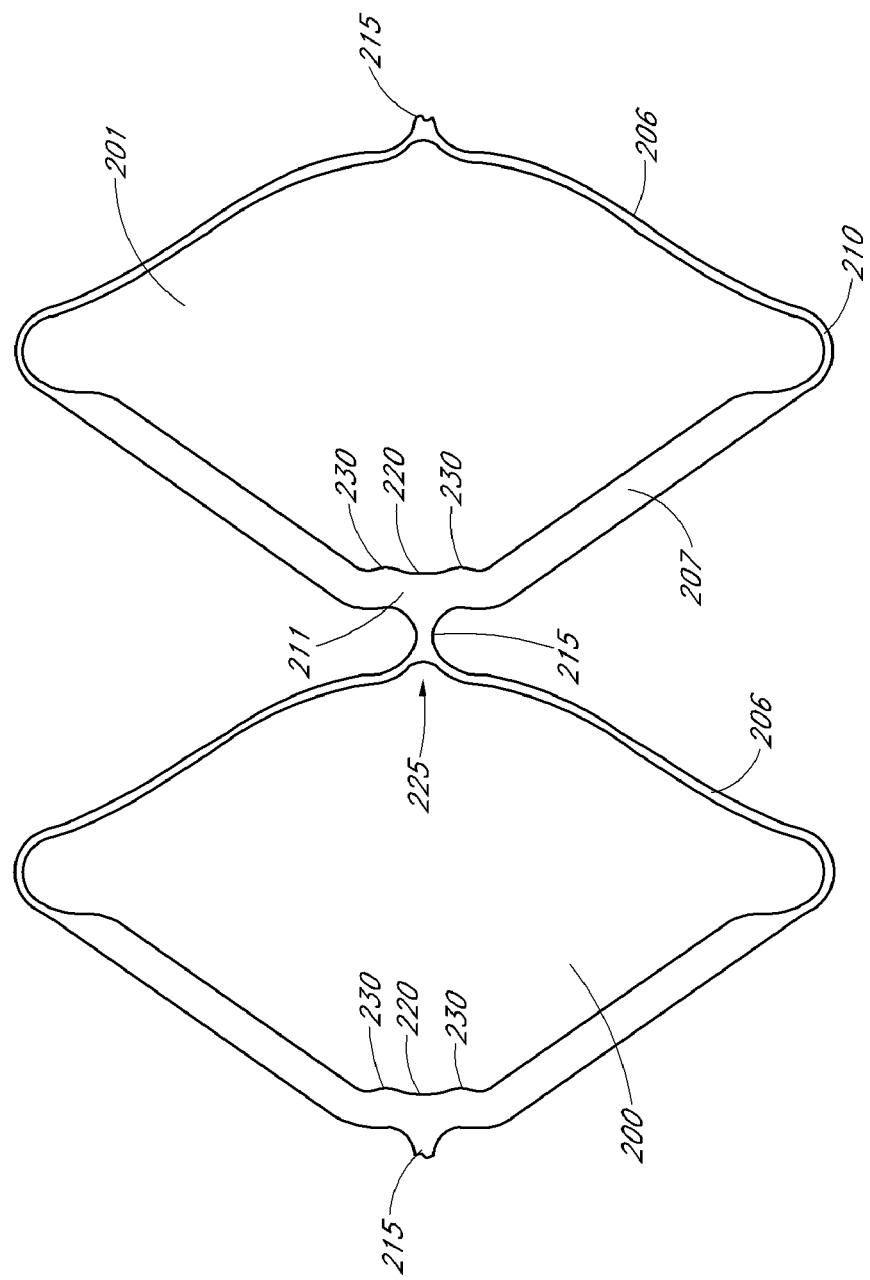
FIG. 16 is a drawing of one embodiment of two cells of a supportive structure having certain features.

Referring to FIG. 16, two unit cells 200, 201 of a device are shown. Such unit cells are demonstrative of certain inventive features of preferred unit cells having thick strut 207 and thin strut 206. These features may also be seen in and are applicable to other figures submitted herewith. One or more of the various features of these unit cells 200, 201 may be used together with one or more other features of units cells described herein (e.g., interconnectors, various width struts).

In this embodiment, thick strut 207 and thin strut 206 are connected at the corners of the unit cell by hinges 210. Hinges 210 are shown as part of the thick strut 207 and thin strut 206. The hinges can take any suitable form, so long as they permit or enhance movement of one more both of the struts 207, 206 about the hinge. In one embodiment, to form hinges 210, the thickness of thick strut 207 is tapered to a thickness approximately equal to the thickness of thin strut 206. In some embodiments, hinge 210 may be formed by a gradual taper of thick strut 207 to a reduced thickness greater than the average thickness of thin strut 206. In certain embodiments, hinge 210 may also be formed by a thin portion of thin strut 206. For example, the hinge portion 210 of thin strut 206 may have a reduced thickness as compared to the average thickness of thin strut 206. As shown, the thickness of thin strut 206 is approximately equal to the thickness of hinge portion 210.

Further referring to FIG. 16, thick strut 206 may comprise a base portion 211. Base portion 211 comprises several notable features. In this embodiment, base portion 211 comprises two convex portions 230, and concave portion 220. In certain embodiments, the base portion is configured to allow substantial resistance to plastic deformation of the thick strut 207. In some embodiments, base portion 211 also includes articulation 215. Articulation 215 is geometrically configured to allow plastic deformation of the individual cells. Articulation 215 creates spacing between thin strut 206 of unit cell 200 and thick strut 207 of unit cell 201. Such spacing provides an area between the thin and thick struts, such that the unit cells may be plastically deformed beyond the predetermined stable collapsed configurations.

Referring to FIG. 17, a stent 240 having a collapsed configuration is shown. Between thin strut 206 and thick strut 207, an articulation 215 is present which allows plastic deformation of stent 240 to a crimped configuration. As shown, stent 240 may be coupled to balloon catheter 501. In certain embodiments, a balloon catheter 501 may be delivered over a guidewire to the body lumen where the stent is to be deployed.

Figure 18B:
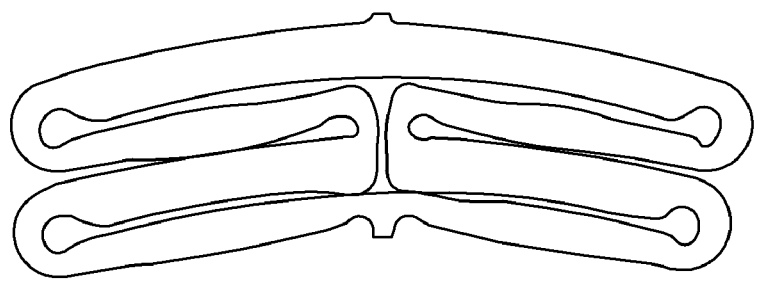
FIGS. 18A-18B are drawings of open cell embodiments having expanded and collapsed configurations.
Figure 18A:
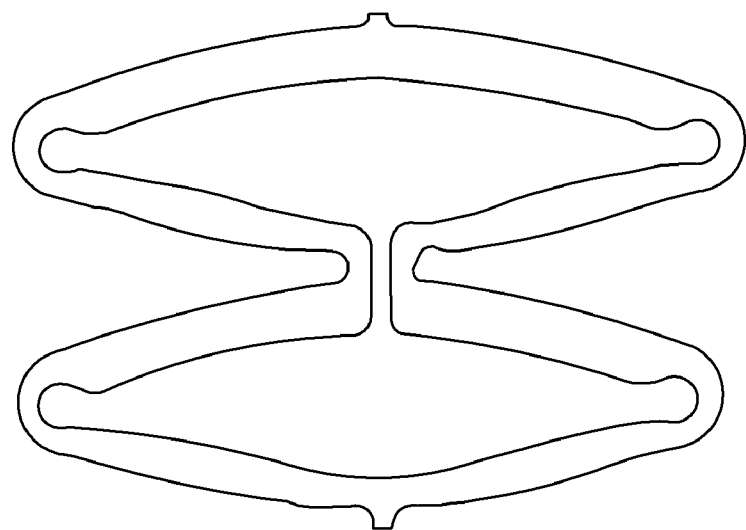

Referring to FIGS. 18A and 18B, one embodiment of a device includes one or more open unit cells. Such devices may include only open cells or a combination of open and closed cells. In certain embodiments, such open unit cells may have a predetermined stable expanded configuration (shown in FIG. 18A) and predetermined stable collapsed configurations. In certain embodiments, such unit cells may also be plastically deformed to collapsed or expanded configurations. In certain embodiments, the various arms of the thin and thick struts may have different stiffness or thicknesses as desired. Designs of open unit cells may be taken to more complicated patterns having various strut undulations and hinge points. Such variables may provide various inversion points which allow certain sections of the open cell to pass through various collapsed or expanded configurations.

Embodiments also include methods of using a medical device having one or more plastically deformable multistable cells. As discussed above, stent 40 may be loaded onto a stent delivery catheter. In some embodiments, the stent is crimped or collapsed onto a stent delivery catheter. In certain embodiments, the stent is collapsed to the predetermined stable collapsed configuration thus decreasing the diameter of the stent.

In certain embodiments, the stent delivery catheter may have a diameter greater than the diameter of the predetermined stable collapsed configuration. If the inner diameter of the collapsed stent is slightly smaller than the outer diameter of the balloon catheter, then the stent would tend to apply radially-inward force on the catheter. This phenomenon may occur as the cells, which have passed the transition point, act under internal forces to attain the predetermined stable configuration. As a result, the stent may "squeeze" the catheter without the need for the further application of an external force.

In some embodiments, the device having one or more unit cells may be crimped further, resulting in some degree of plastic deformation beyond the collapsed configuration. In certain embodiments, a stent may be plastically deformed to a collapsed configuration having a smaller diameter than the predetermined stable collapsed configuration. Advantageously, such stent designs allow for a smaller deployment diameter of the stent. Moreover, the stent may substantially maintain its smaller diameter stent profile upon plastic deformation, as the stent exhibits reduced recoil when compared to stents of different designs.

Once coupled to the delivery device, a user may optionally place a sheath or other external barrier around device 40. It will be appreciated that in some embodiments of the present invention, such a sheath is not desirable, as it may unnecessarily increase the delivery profile.

Once positioned on the delivery device, the medical device may then be inserted into a body lumen. The medical device may be delivered to a desired deployment location within a blood vessel or other passageway. Once in the desired location, the medical device may be deployed.

Deployment of the medical device may occur in various fashions depending on the medical device and the delivery device. In certain embodiments, the delivery device provides a radial outward force on the medical device. Such force is sufficient to transition one or more unit cells to a stable expanded configuration. In certain embodiments, the stable expanded configuration is the predetermined stable expanded configuration.

In some embodiments, the delivery device may disengage the medical device once expanded to the predetermined stable expanded configuration. A user optionally may adjust the position of device 40 in the passageway while in a predetermined stable collapsed or expanded configuration, depending on the size of the passageway.

In certain embodiments, a multistable medical device having two or more stable expanded configurations, which are not plastically deformed expanded configurations, may be used. The medical device may be deployed in any of the stable expanded configurations. In some embodiments, the medical device having one or more cells may be expanded in a manner that results in a varied diameter along its length. For example, the balloon may be deflated and repositioned, or another balloon may be expanded at a location within device 40, such that a force is applied to only a portion of device. As such, an area of device 40 may be expanded to a larger diameter than another area of device 40.

In certain embodiments, the delivery device may be used to apply a force sufficient to plastically deform the medical device from a predetermined stable expanded configuration to a plastically deformed stable expanded configuration. In certain embodiments, the delivery device applies a force to the medical device through mechanical means. In some embodiments, a balloon may be inflated to apply a radially-outward force on device 40 and expand the diameter of device 40. In certain embodiments, the stent may be plastically deformed such that the stent contacts and/or supports the passageway.

Once the device has been plastically deformed and expanded into a desired configuration, the catheter may be removed from the patient, leaving device 40 to support the passageway. Placement of device 40 may be ascertained at this time, or earlier, by radiography or other known methods.

The stents and other medical devices described herein may be used together with other known options and methods. For example, drugs optionally may be combined with a stent having the design described herein by coating the stent or using other known methods. One of skill in the art will appreciate that stents and other medical devices may also comprise a coating, such as a coating of one or more drugs, medications, or polymers. In particular embodiments, the medical device (e.g., stent) including the unit cells may be coated with a crosslinked collagen protein coating. Such stent would possess the clinical benefits of being less thrombogenic and provide a medium for endothelium cell migration across the device. In certain embodiments, a tie layer may be used to tie the coating to the unit cells.

As an example of the results obtainable by the present invention, the following information is provided based in experiments that have been conducted. A coronary stent constructed in accordance with the present invention was formed having an outer diameter of 1.8 mm when in the expanded predetermined stable configuration. This stent was crimped to a collapsed configuration having an outer diameter of 0.8 mm. Then, the stent was expanded to a point in which plastic deformation occurred. The final diameter of the stent was measured to be 3.0 mm. Thus, one of skill in the art will appreciate the relationship between the compact delivery profile and the attainable expanded diameter of this stent.

The various methods and techniques described above provide a number of ways to carry out the invention. Of course, it is to be understood that not necessarily all objectives or advantages described may be achieved in accordance with any particular embodiment described herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A method of crimping a lumen support on a delivery device comprising:
    delivering a lumen support onto a delivery device, the lumen support comprising one or more unit cells, the one or more unit cells having a thick strut and a thin strut and capable of assuming an original collapsed configuration or a plastically deformed collapsed configuration and an original expanded configuration or a plastically deformed expanded configuration, wherein no stable configurations exist between the original collapsed configurations or the original expanded configuration;
    applying a radially inward force to the lumen support; and
    deforming one or more unit cells of the lumen support to a plastically deformed collapsed configuration.

2. The method of claim 1, further comprising transitioning the lumen support to a stable collapsed configuration from a stable expanded configuration by application of a force through an inversion point of decreased force.

3. The method of claim 1, wherein lumen support has a smaller diameter in the plastically deformed collapsed configuration.

4. The method of claim 1, wherein the thin strut is more pliable than the thick strut.

5. The method of claim 1, wherein the lumen support comprises a material having an elastic range between about 0.15 to about 1% and an elongation of about 30% and an ultimate tensile strength greater than 500 MPa.

6. The method of claim 5, wherein the material is a cobalt alloy.

7. The method of claim 1, wherein the support comprises first flexible articulations and an interconnector configured to allow one or more unit cells of a first column to conform to a lumen.

8. The method of claim 7, wherein the first flexible articulations are configured to geometrically change an amount of force required to reach an inversion point of the unit cell.

9. The method of claim 7, wherein the interconnector displaces adjacent columns relative to one another.

10. The method of claim 7, wherein the interconnector is configured for better nesting of one or more unit cells in the original collapsed configuration or plastically deformed collapsed configuration.

11. The method of claim 7, wherein the interconnect extends along the thin strut and bends in a direction substantially parallel to an axis of a column of unit cells in the lumen support.

12. The method of claim 7, wherein the interconnect extends along the thick strut and joins the first flexible articulation of a unit cells in an adjacent row of the lumen support.

13. The method of claim 1, wherein the thin strut substantially conforms to the shape of the thick struck in the original collapsed configuration.

14. The method of claim 1, wherein the plastically deformed collapsed configuration reduces the area of the unit cell.

15. The method of claim 1, wherein the step of deforming the one or more or more unit cells decreases a distance from the thin strut to the thick strut.

16. The method of claim 1, wherein the lumen support comprises a medical device selected from the group consisting of a stent, an occlusion device, a multistable valve, an expander, a clip, a loop, and a ring.

* * * * *